US010018824B2

(12) United States Patent
Reed

(10) Patent No.: US 10,018,824 B2
(45) Date of Patent: Jul. 10, 2018

(54) TEMPORAL COMPRESSIVE SENSING SYSTEMS

(71) Applicant: Integrated Dynamic Electron Solutions, Inc., Pleasanton, CA (US)

(72) Inventor: Bryan W. Reed, San Leandro, CA (US)

(73) Assignee: INTEGRATED DYNAMIC ELECTRON SOLUTIONS, INC., Pleasanton, CA (US)

( * ) Notice: Subject to any disclaimer, the term of this patent is extended or adjusted under 35 U.S.C. 154(b) by 0 days.

(21) Appl. No.: 15/802,876

(22) Filed: Nov. 3, 2017

(65) Prior Publication Data

US 2018/0136449 A1 May 17, 2018

Related U.S. Application Data

(62) Division of application No. 15/243,235, filed on Aug. 22, 2016, now Pat. No. 9,841,592.

(60) Provisional application No. 62/258,194, filed on Nov. 20, 2015.

(51) Int. Cl.

| G01N 23/00 | (2006.01) |
| G02B 21/36 | (2006.01) |
| G06T 11/00 | (2006.01) |
| H01J 37/22 | (2006.01) |
| H01J 37/28 | (2006.01) |

(Continued)

(52) U.S. Cl.
CPC ......... *G02B 21/365* (2013.01); *G01N 23/225* (2013.01); *G06T 11/003* (2013.01); *H01J 37/222* (2013.01); *H01J 37/265* (2013.01); *H01J 37/28* (2013.01); *H01J 2237/221* (2013.01); *H01J 2237/226* (2013.01); *H01J 2237/24455* (2013.01); *H01J 2237/262* (2013.01); *H01J 2237/2802* (2013.01)

(58) Field of Classification Search
CPC ............... H01J 37/28; H01J 2237/2817; H01J 2237/30483; H01J 37/302; A61B 8/5207
See application file for complete search history.

(56) References Cited

U.S. PATENT DOCUMENTS

| 7,511,643 B2 | 3/2009 | Baraniuk et al. |
| 7,646,924 B2 | 1/2010 | Donoho et al. |
| 7,834,795 B1 | 11/2010 | Dudgeon et al. |

(Continued)

FOREIGN PATENT DOCUMENTS

WO WO-2017087045 A1 5/2017

OTHER PUBLICATIONS

Arguello, et al. Code aperture design for compressive spectral imaging. In Signal Processing Conference, 2010 18th European. IEEE. Aug. 2010:1434-38.

(Continued)

*Primary Examiner* — Kenneth J Malkowski
(74) *Attorney, Agent, or Firm* — Wilson Sonsini Goodrich & Rosati

(57) ABSTRACT

Methods and systems for temporal compressive sensing are disclosed, where within each of one or more sensor array data acquisition periods, one or more sensor array measurement datasets comprising distinct linear combinations of time slice data are acquired, and where mathematical reconstruction allows for calculation of accurate representations of the individual time slice datasets.

12 Claims, 9 Drawing Sheets

(51) Int. Cl.
    H01J 37/26      (2006.01)
    G01N 23/225     (2018.01)

(56) References Cited

U.S. PATENT DOCUMENTS

| | | | |
|---|---|---|---|
| 8,199,244 | B2 | 6/2012 | Baraniuk et al. |
| 8,458,109 | B2 | 6/2013 | Zhang et al. |
| 8,559,688 | B2 | 10/2013 | Khare et al. |
| 8,687,689 | B2 | 4/2014 | Baraniuk et al. |
| 8,933,401 | B1* | 1/2015 | Reed ............ H01J 37/28 250/306 |
| 9,165,743 | B2 | 10/2015 | Reed et al. |
| 9,841,592 | B2 | 12/2017 | Reed |
| 2012/0038786 | A1* | 2/2012 | Kelly ............ G02B 26/0833 348/222.1 |
| 2012/0203810 | A1 | 8/2012 | Ashikhmin |
| 2012/0314099 | A1 | 12/2012 | Kelly et al. |
| 2013/0070138 | A1 | 3/2013 | Baraniuk et al. |
| 2015/0153227 | A1 | 6/2015 | Shi et al. |
| 2016/0276129 | A1* | 9/2016 | Stevens ............ G03F 7/20 |

OTHER PUBLICATIONS

Asif, et al. Streaming compressive sensing for high-speed periodic videos. In 2010 IEEE International Conference on Image Processing. IEEE. Sep. 2010:3373-76.

Bach, et al. Sparse coding and dictionary learning for image analysis. Part II: Dictionary learning for signal reconstruction. ICCV'09 tutorial, Kyoto, Sep. 28, 2009:1-43.

Baraniuk, et al. Tutorial: Compressive Sensing of Video. CVPR 2012, Providence, Rhode Island, USA, Jun. 16, 2012:1-105.

Baraniuk, R. Compressive sensing. IEEE Signal Processing Magazine. 2007; 24(4):118-121.

Bruckstein, et al. From sparse solutions of systems of equations to sparse modeling of signals and images. SIAM Review. 2009; 51(1):34-81.

Candes, et al. $\ell$1-magic: Recovery of sparse signals via convex programming. URL:www.acm.caltech.edu/l1magic/downloads/l1magic.pdf, 4, 14 (2005).

Candes, et al. Near-optimal signal recovery from random projections: Universal encoding strategies?. IEEE transactions on information theory. 2006; 52(12):5406-25.

Candes, et al. Robust uncertainty principles: Exact signal reconstruction from highly incomplete frequency information. IEEE Transactions on information theory. 2006; 52(2):489-09.

Candes, et al. Sparsity and incoherence in compressive sampling. Inverse Problems. 2007; 23(3):969.

Candes, et al. Stable signal recovery from incomplete and inaccurate measurements. Communications on Pure and Applied Mathematics. 2006; 59(8):1207-23.

Castro, et al. Compressed sensing vs. active learning. In 2006 IEEE International Conference on Acoustics Speech and Signal Processing Proceedings. IEEE. May 2006; vol. 3:III-III.

Chen, et al. Compressed sensing and dictionary learning. Proceed. Symp. Applied Math. 73:201-241, 2016. (Preprint 106 available online: 2015:1-41).

Cormen, et al. Chapter 16: Greedy algorithms. Introduction to Algorithms Third Edition, MIT Press, Cambridge, MA, 2009 (38 pgs).

Coulter, et al. Adaptive compressed sensing—a new class of self-organizing coding models for neuroscience. In 2010 IEEE International Conference on Acoustics, Speech and Signal Processing. IEEE. Mar. 2010:5494-97.

Donoho, David L. For most large underdetermined systems of linear equations the minimal $\ell$ 1-norm solution is also the sparsest solution. Communications on Pure and Applied Mathematics. 2006; 59(6):797-829.

Duarte, et al. Kronecker compressive sensing. IEEE Transactions on Image Processing. 2012; 21(2): 494-504.

Duarte, et al. Single-pixel imaging via compressive sampling. IEEE Signal Processing Magazine. 2008; 25(2):83-91.

Egiazarian, et al. Compressed sensing image reconstruction via recursive spatially adaptive filtering. In 2007 IEEE International Conference on Image Processing. IEEE. Sep. 2007; vol. 1:I-549.

Gu, et al. Compressive structured light for recovering inhomogeneous participating media. In European Conference on Computer Vision. Springer Berlin Heiderlberg. Oct. 2008:845-58.

Harmany, et al. Sparse Poisson intensity reconstruction algorithms. In 2009 IEEE/SP 15th Workshop on Statistical Signal Processing. IEEE. Aug. 2009:634-37.

Hayashi, et al. A user's guide to compressed sensing for communications systems. IEICE transactions on communications. 2013; 96(3):685-712.

Huang, et al. Bayesian nonparametric dictionary learning for compressed sensing MRI. IEEE Transactions on Image Processing. 2014; 23(12):5007-19.

International Search Report and Written Opinion dated Oct. 28, 2016 for International PCT Patent Application No. PCT/US2016/048087.

Ji, et al. Bayesian compressive sensing. IEEE Transactions on Signal Processing. 2008; 56(6):2346-56.

Kreutz-Delgado, et al. Dictionary learning algorithms for sparse representation. Neural Computation. 2003;15(2):349-96.

Llull, et al. Coded aperture compressive temporal imaging. Optics Express. 2013; 21(9):10526-45.

Marim, et al. Compressed sensing with off-axis frequency-shifting holography. Optics letters. 2010; 35(6): 871-73.

Notice of Allowance dated Aug. 25, 2017 for U.S. Appl. No. 15/243,235.

Office Action dated Apr. 4, 2017 for U.S. Appl. No. 15/243,235.

Paisley, et al. Nonparametric factor analysis with beta process priors. In Proceedings of the 26th Annual International Conference on Machine Learning, 2009 (pp. 777-784). International Conference on Machine Learning (ICML), Montreal, Canada, 2009.

Pennycook, et al. Efficient phase contrast imaging in STEM using a pixelated detector. Part 1: Experimental demonstration at atomic resolution. Ultramicroscopy. 2015; 151:160-167.

Sawatzky, et al. Total variation processing of images with Poisson statistics. In International Conference on Computer Analysis of Images and Patterns. Springer Berlin Heidelberg. Sep. 2009: 533-40.

Scheres, S. Relion: Implementation of a Bayesian Approach to Cryo-EM Structure Determination. Journal of Structural Biology. 2012; 180(3):519-30.

Shankar, et al. Compressive video sensors using multichannel imagers. Applied optics. 2010; 49(10): B9-17.

Soni, et al. Learning sparse representations for adaptive compressive sensing. In 2012 IEEE International Conference on Acoustics, Speech and Signal Processing (ICASSP). IEEE. Mar. 2012: 2097-100.

Stevens, et al. Applying compressive sensing to TEM video: a substantial frame rate increase on any camera. Advanced Structural and Chemical Imaging. 2015; 1(10):1-20.

Takhar, et al. A new compressive imaging camera architecture using optical-domain compression. In Electronic Imaging 2006. International Society for Optics and Photonics. Feb. 2006:606509-606509.

Tsai, et al. Coded aperture compressive spectral-temporal imaging. Computational Optical Sensing and Imaging, Jun. 7-11, 2015 (paper CTh2E-5).

Wagadarikar, et al. Single disperser design for coded aperture snapshot spectral imaging. Applied optics. 2008; 47(10):B44-51.

Wagadarikar, et al. Video rate spectral imaging using a coded aperture snapshot spectral imager. Optics Express. 2009; 17(8):6368-88.

Weinstein, A. Beginners Code for Compressive Sensing. Sep. 2009:1-6.

Willett, et al. Compressed sensing for practical optical imaging systems: a tutorial. Optical Engineering. 2011; 50(7):072601-1 thru 072601-13.

Willett, et al. Performance bounds on compressed sensing with Poisson noise. In 2009 IEEE International Symposium on Information Theory. IEEE. Jun. 2009:174-78.

(56) References Cited

OTHER PUBLICATIONS

Yang, et al. A Review of Fast ℓ1-Minimization Algorithms for Robust Face Recognition. International Conference of Image Processing, 2010, pp. 1849-1852.

Yang, et al. Video compressive sensing using Gaussian mixture models. IEEE Transactions on Image Processing. 2014; 23(11):4863-78.

Ye, et al. Compressive confocal microscopy. In 2009 IEEE International Conference on Acoustics, Speech and Signal Processing. IEEE. Apr. 2009: 429-432.

Yuan, et al. Adaptive temporal compressive sensing for video. In 2013 IEEE International Conference on Image Processing. IEEE. Sep. 2013:14-18.

Yuan, et al. Low-cost compressive sensing for color video and depth. In Proceedings of the IEEE Conference on Computer Vision and Pattern Recognition. 2014:3318-25.

Zhou, et al. Nonparametric Bayesian dictionary learning for analysis of noisy and incomplete images. IEEE Transactions on Image Processing. 2012; 21(1):130-44.

Zhou, et al. Non-parametric Bayesian dictionary learning for sparse image representations. In Advances in Neural Information Processing Systems 22. 2009:2295-2303.

\* cited by examiner

TEMPORAL COMPRESSIVE SENSING SYSTEMS

CROSS-REFERENCE

This application is a Divisional Application which claims the benefit of U.S. application Ser. No. 15/243,235, filed Aug. 22, 2016, which claims the benefit of U.S. Provisional Application No. 62/258,194, filed on Nov. 20, 2015, each of which application is incorporated herein by reference in its entirety.

STATEMENT AS TO FEDERALLY SPONSORED RESEARCH

This invention was made with the support of the United States government under Award number DE-SC0013104 by the United States Department of Energy.

BACKGROUND

Compressive sensing is an approach to signal acquisition and processing that makes use of the inherent properties of some signals to measure and mathematically reconstruct the signal based on a limited series of test measurements. This disclosure relates to novel systems and methods for temporal compressive sensing. For example, one specific disclosure is related to novel temporal compressive sensing systems and methods as applied to a transmission electron microscope (TEM).

SUMMARY

Disclosed herein are methods for temporal compressive sensing, comprising: a) directing radiation having an intensity from a source towards a sample or scene; b) capturing sensor array data for one or more data acquisition periods, wherein within each of the one or more data acquisition periods, one or more measurement datasets corresponding to distinct linear combinations of patterns of the radiation transmitted, reflected, elastically scattered, or inelastically scattered by the sample or scene are captured for a series of time slices; and c) reconstructing a time slice dataset for each of the time slices of the series within each of the one or more data acquisition periods using: i) the one or more measurement datasets captured for each data acquisition period; ii) a series of coefficients that describe a known time-dependence of the intensity of the radiation from the source that is directed to the sample or scene within the data acquisition period, or a known time-dependence for switching the radiation transmitted, reflected, elastically scattered, or inelastically scattered by the sample or scene to different regions of the sensor array within the data acquisition period, wherein the coefficients vary as a function of time slice and region of the sensor array but are independent of the spatial position for a given pixel within the sensor array or within a given region of the sensor array; and iii) an algorithm that calculates the time slice datasets from the one or more measurement datasets captured for each data acquisition period and the series of coefficients; thereby providing a series of time slice datasets for each of the one or more data acquisition periods that has a time resolution exceeding the time resolution determined by the length of the data acquisition period.

In some embodiments, the sensor array is a two-dimensional sensor array comprising a charge-coupled device (CCD) sensor, a complementary metal oxide semiconductor (CMOS) sensor, a CMOS framing camera, a photodiode array, or any combination thereof. In some embodiments, the sensor array further comprises a nonlinear optical material, a fluorescent material, a phosphorescent material, or a micro-channel plate, that converts the radiation into radiation directly detectable by the sensor array. In some embodiments, the algorithm used to reconstruct the time slice datasets is an optimization algorithm that penalizes non-sparse solutions of an underdetermined system of linear equations via the l1 norm, the total number of non-zero coefficients, total variation, or beta process priors; an iterative greedy recovery algorithm; a dictionary learning algorithm; a stochastic Bayesian algorithm; a variational Bayesian algorithm; or any combination thereof. In some embodiments, at least or at least about 10 time slice datasets are reconstructed from the one or more measurement datasets captured for each data acquisition period. In some embodiments, the two-dimensional sensor array operates at an effective data acquisition and read-out rate of at least or at least about 100 frames per second. In some embodiments, the radiation comprises electrons, and wherein the sensor array is a charge-coupled device (CCD) sensor, an image-intensified charge-coupled device (ICCD) sensor, the detector in an electron energy loss spectrometer (EELS), or any combination thereof. In some embodiments, the radiation comprises electrons and the sensor array is replaced by the detector in an energy-dispersive x-ray spectrometer (EDX). In some embodiments, the time slice data sets comprise reconstructed frames of transmission electron microscope image data, transmission electron microscope diffraction pattern data, transmission electron microscope electron energy loss spectral data, transmission electron microscope energy-dispersive x-ray spectral data, or scanning electron microscope image data. In some embodiments, the number of time slice datasets to be reconstructed is adjusted during the calculation of the time slice datasets. In some embodiments, the number of time slice datasets to be reconstructed is optimized by calculating a range of measurement matrix coefficients, each with a different number of time slices, prior to capturing the measurement datasets. In some embodiments, the distinct linear combinations of patterns of the radiation transmitted, reflected, elastically scattered, or inelastically scattered by the sample or scene for a series of time slices are generated by modulating in a temporal fashion an experimental parameter other than the radiation intensity. In some embodiments, the experimental parameter to be temporally modulated is selected from the group consisting of rotational orientation of the sample or scene, linear translation of the sample or scene in one dimension, linear translation of the sample or scene in two dimensions, and linear translation of the sample or scene in three dimensions, or any combination thereof. In some embodiments, the radiation is focused to a narrow beam and the experimental parameter to be temporally modulated is the position of the beam relative to the sample or scene. In some embodiments, the series of coefficients describe a known spatial-dependence and time-dependence of the intensity of the radiation from the source that is directed towards the sample or scene within the data acquisition period, or a known spatial-dependence of the intensity of the radiation from the source and a known time-dependence for switching the radiation transmitted, reflected, elastically scattered, or inelastically scattered by the sample or scene to different regions of the sensor array within the data acquisition period.

Also disclosed herein are systems for temporal compressive sensing, comprising: a) a radiation source that provides radiation having an intensity directed towards a sample or scene; b) a sensor array that detects the radiation subsequent to transmission, reflection, elastic scattering, or inelastic scattering by the sample or scene; c) a mechanism that rapidly modulates the intensity of the radiation generated by the radiation source prior to its interaction with the sample or scene, or that rapidly switches the radiation transmitted, reflected, elastically scattered, or inelastically scattered by the sample or scene to different regions of the sensor array, and d) one or more computer processors that: (i) capture sensor array data for one or more data acquisition periods, wherein within each data acquisition period, one or more measurement datasets corresponding to distinct linear combinations of patterns of transmitted, reflected, elastically scattered, or inelastically scattered radiation for a series of time slices are captured; and (ii) reconstruct a time slice dataset for each time slice within each of the one or more data acquisition periods using: 1) the one or more measurement datasets captured for each data acquisition period; 2) a series of coefficients that describe a known time-dependence of the intensity of the radiation generated by the radiation source and directed to the sample or scene within the data acquisition period, or a known time-dependence for switching the radiation transmitted, reflected, elastically scattered, or inelastically scattered by the sample or scene to different regions of the sensor array within the data acquisition period, and wherein the coefficients vary as a function of time slice and region of the sensor array but are independent of the spatial position for a given pixel within the sensor array or within a given region of the sensor array; and 3) an algorithm that calculates the time slice datasets from the one or more measurement datasets captured for each data acquisition period and the series of coefficients; thereby generating a series of time slice datasets for each of the one or more data acquisition periods that has a time resolution exceeding the time resolution determined by the length of the data acquisition period.

In some embodiments, the radiation source is a laser, a photocathode, an electron gun, or any combination thereof. In some embodiments, the sensor array is a two-dimensional sensor array comprising a charge-coupled device (CCD) sensor, a complementary metal oxide semiconductor (CMOS) sensor, a CMOS framing camera, a photodiode array, or any combination thereof. In some embodiments, the sensor array further comprises a nonlinear optical material, a fluorescent material, a phosphorescent material, or a micro-channel plate, that converts the signal from the radiation source of claim 1 into radiation directly detectable by the sensor array. In some embodiments, the algorithm that reconstructs the time slice datasets is an optimization algorithm that penalizes non-sparse solutions of an underdetermined system of linear equations via the 11 norm, the total number of non-zero coefficients, total variation, or beta process priors, an iterative greedy recovery algorithm, a dictionary learning algorithm, a stochastic Bayesian algorithm, a variational Bayesian algorithm, or any combination thereof. In some embodiments, at least or at least about 10 time slice datasets are reconstructed from the one or more measured datasets captured for each data acquisition period. In some embodiments, the two-dimensional sensor array operates at an effective data acquisition and read-out rate of at least or at least about 100 frames per second. In some embodiments, the radiation comprises electrons and the sensor array is a charge-coupled device (CCD) sensor, an image-intensified charge-coupled device (ICCD) sensor, the detector in and electron energy loss spectrometer (EELS), or any combination thereof. In some embodiments, the radiation comprises electrons and the sensor array is replaced by the detector in an energy-dispersive x-ray spectrometer (EDX). In some embodiments, the time slice data sets comprise reconstructed frames of transmission electron microscope image data, transmission electron microscope diffraction pattern data, transmission electron microscope electron energy loss spectral data, transmission electron microscope energy-dispersive x-ray spectral data, or scanning electron microscope image data. In some embodiments, the number of time slice datasets to be reconstructed is adjusted during the calculation of the time slice datasets. In some embodiments, the number of time slice datasets to be reconstructed is optimized by calculating a range of measurement matrix coefficients, each with a different number of time slices, prior to capturing the measurement datasets. In some embodiments, the series of coefficients describe a known spatial-dependence and time-dependence of the intensity of the radiation from the source that is directed towards the sample or scene within the data acquisition period, or a known spatial-dependence of the intensity of the radiation from the source and a known time-dependence for switching the radiation transmitted, reflected, elastically scattered, or inelastically scattered by the sample or scene to different regions of the sensor array within the data acquisition period.

Disclosed herein are systems for temporal compressive sensing, comprising: a) a radiation source that provides radiation directed towards a sample or scene; b) a sensor array that detects the radiation subsequent to transmission, reflection, elastic scattering, or inelastic scattering by the sample or scene; c) a mechanism that rapidly modulates the one-, two-, or three-dimensional translational position or rotational orientation of the sample or scene relative to the direction of irradiation; and d) one or more computer processors that: (i) capture sensor array data for one or more data acquisition periods, wherein within each data acquisition period, one or more measurement datasets corresponding to distinct linear combinations of patterns of transmitted, reflected, elastically scattered, or inelastically scattered radiation for a series of time slices are captured; and (ii) reconstruct a time slice dataset for each time slice within each of the one or more data acquisition periods using: 1) the one or more measurement datasets captured for each data acquisition period; 2) a series of coefficients that describe a known time-dependence of the translational position or rotational orientation of the sample or scene within the data acquisition period; and 3) an algorithm that calculates the time slice datasets from the one or more measurement datasets captured for each data acquisition period and the series of coefficients; thereby generating a series of time slice datasets for each of the one or more data acquisition periods that has a time resolution exceeding the time resolution determined by the length of the data acquisition period.

In some embodiments, the radiation is focused to a narrow beam and the mechanism rapidly modulates the position of the beam relative to the sample or scene.

INCORPORATION BY REFERENCE

All publications, patents, and patent applications mentioned in this specification are herein incorporated by reference in their entirety to the same extent as if each individual publication, patent, or patent application was specifically and individually indicated to be incorporated by reference in their entirety. In the event of a conflict between a term herein and a term in an incorporated reference, the term herein controls.

BRIEF DESCRIPTION OF THE DRAWINGS

The following description and examples illustrate embodiments of the invention in detail. It is to be understood that this invention is not limited to the particular embodiments described herein and as such may vary. Those of skill in the art will recognize that there are numerous variations and modifications of this invention, which are encompassed within its scope.

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 4 illustrates that the data in FIG. 1 is compressible, requiring only four measured images to reconstruct all ten distinct images representing the state of the sample in each time slice.

DETAILED DESCRIPTION

Figure 1:
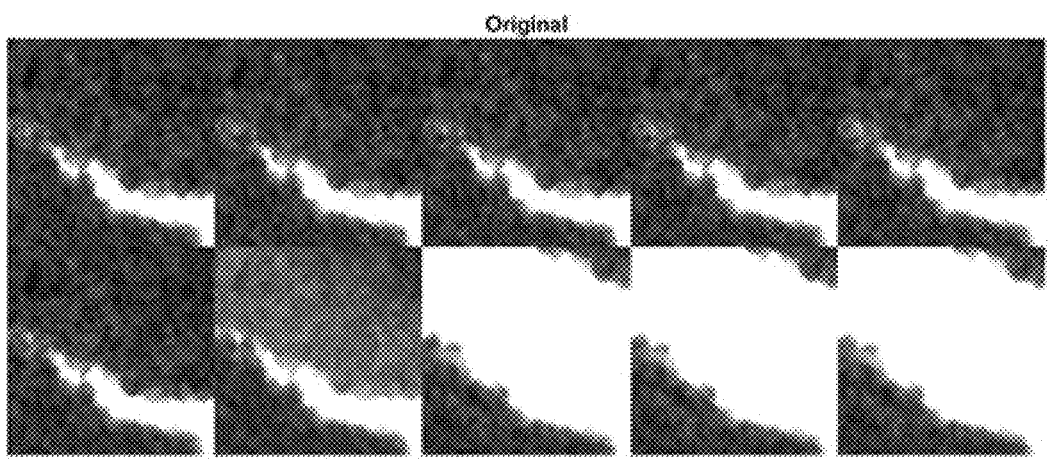
FIG. 1 illustrates 10 frames of TEM image data from an in situ tensile crack propagation experiment (courtesy K. Hattar et al., Sandia National Laboratory).

Overview of Compressive Sensing:

Compressive sensing (also known as compressed sensing, compressive sampling, or sparse sampling) is a family of signal acquisition and processing techniques for efficiently acquiring and reconstructing a signal. As used herein, the term "signal" and its grammatical equivalents includes, but is not limited to, intensity, frequency, or phase data as it pertains to an electrical, electromagnetic, or magnetic field, as well as to optical or non-optical image data, spectral data, diffraction data, and the like. In compressive sensing, reconstruction of a signal is performed by making a limited number of signal measurements according to a defined set of sampling functions (or test functions), and subsequently finding mathematical solutions to the resulting system of linear equations that relate the unknown "true" signal to the set of measured values. Reconstruction thus provides an estimate of the "true" signal, the accuracy of which is dependent on several factors including, but not limited to, properties of the signal itself, the choice of test functions used to sample the signal, the amount of noise in the signal, and the mathematical algorithm selected to solve the system of linear equations. Because the signal is under-sampled, the system of linear equations is underdetermined (i.e., has more unknowns than equations). In general, underdetermined systems of equations have an infinite number of solutions. The compressive sensing approach is based on the principle that prior knowledge of or reasonable assumptions about the properties of the signal can be exploited to recover it from far fewer sampling measurements than would be required by conventional Nyquist-Shannon sampling. Two conditions must be satisfied for accurate reconstruction of compressively sensed signals: (i) the signal must be "sparse" in some domain (i.e., the signal may be represented in some N-dimensional coordinate system as a linear combination of basis vectors, where only a small number, K, of the coefficients for each of the basis vectors are non-zero (K<<N)), and (ii) the signal and sampling measurement functions must be incoherent (i.e., the set of measurement functions (vectors) are randomly distributed across the set of N basis vectors for the domain in which the signal is sparse).

Many real world signals, e.g., photographic images and video data, exhibit underlying structure and redundancy that satisfy the sparsity and incoherence conditions in an appropriately selected domain. Data compression and decompression algorithms used to produce mpeg and jpeg files exploit essentially the same concept as that used in compressive sensing to reduce the amount of data storage required or to facilitate data transmission. However, these signal processing algorithms are applied post-signal acquisition. Compressive sensing is applied at the signal acquisition stage to improve the efficiency of data capture as well as to reduce data storage and transmission requirements.

In compressive sensing, a system of linear equations is generated through acquisition of a series of sampling measurements performed using a set of known test functions, where the total number of sampling measurements, M, is small compared to the number required by Nyquist-Shannon sampling theory but where the sampled data still contains essentially all useful information contained in the original signal. This linear system of equations is often expressed as:

$$y(m) = \Phi x(n) = \Phi \Psi \alpha \qquad (1)$$

where $y(m)$, $m=1, M$ represents the sampling measurements, $x(n)$, $n=1, 2, N$ represents the values of the unknown signal, $\Phi$ is an M×N matrix representing the known weighting factors (test functions) used to acquire the sampling measurements (the latter comprising linear combinations of the products of the weighting factors and the signal coefficients for the chosen set of basis vectors), and $\Psi$ and $\alpha$ represent the basis vectors and corresponding coefficients respectively of the N-dimensional coordinate system in which the signal, x(n), may be represented as $x(n)=\Sigma_{i=1}^{N} \alpha_i \Psi_i$. Solving equation (1) for the unknown values of x(n) thus corresponds to solving the underdetermined system of linear equations. As indicated above, underdetermined systems of linear equations have an infinite number of solutions, however, imposing the constraints of sparsity and incoherence limits the possible solutions to those having a small (or minimum) number of non-zero coefficients, and enables one to reconstruct the original signal with a high degree of accuracy. A variety of mathematical approaches exist for solving this problem including, but not limited to, optimization of the $l_1$ norm, greedy algorithms, stochastic Bayesian algorithms, variational Bayesian algorithms, and dictionary learning algorithms.

Video Compressive Sensing:

The compressive sensing literature includes application areas ranging from optical imaging to magnetic resonance imaging to spectroscopy and others. Temporal compressive sensing methods, i.e., in which signals are reconstructed using data sets that under-sample the signal in the time domain, have been applied primarily, but not exclusively, to video compression. Typically these methods utilize some form of a jittered, random-coded aperture that is physically moved (usually with a piezoelectric system) on a time scale much shorter than the acquisition time for a single video frame, thereby spatially encoding the sampling measurements. Thus, in effect, the datum for each pixel in the acquired video frame represents a different linear combination of light intensities sampled at different points in time. Mathematical reconstruction is used to calculate the video image that would have been observed at each of the referenced points in time if the frame rate or data acquisition time for the camera had been faster. In favorable cases, variants of the standard algorithms described in the compressive sensing literature can be used to reconstruct tens or even hundreds of reconstructed frames of video data from a single such data acquisition period. This type of compressive sensing system has been demonstrated for optical video cameras, and researchers are currently attempting to apply the same approach to compressive sensing in transmission electron microscopes (TEMs).

Video Compressive Sensing as Applied to Electron Microscopy:

The difficulties of producing the required coded aperture, inserting it at an appropriate place in the electron beam path, preventing it from accumulating contamination or being damaged upon exposure to the electron beam, and moving it inside the vacuum system with the required speed, precision, and repeatability have reportedly been substantial (see the recently published paper by Stevens et al., (2015), "Applying Compressive Sensing to TEM Video: a Substantial Frame Rate Increase on any Camera", Adv. Structural and Chemical Imaging 1:10, for a description of the computational and mathematical aspects of the approach). The practical limitations of implementing coded-aperture video compressive sensing in a TEM have been and will continue to be substantial. The system modifications required to implement coded-aperture video compression can be both expensive and highly invasive, and may require frequent (and potentially difficult) maintenance and recalibration steps. The practicality of this approach will thus likely be limited by physical considerations (charging, contamination, limited resolution, etc.) not accounted for in the published computational study.

U.S. Pat. No. 8,933,401 describes an alternative implementation of compressive sensing in an electron microscope system (including either a TEM or a scanning electron microscope (SEM)) in which a spatial pattern of electron-illumination intensity (or "mask") is produced at a sample, and the microscope captures information (including, but not limited to, image intensity data, diffraction patterns, electron energy-loss spectra (EELS), or energy-dispersive X-ray spectra (EDX)) using a two-dimensional sensor array comprising N spatial pixels from the superposition of measurements at spatial positions defined by the mask. Rather than using a coded aperture to control the spatial variation of electron-illumination intensity, this approach makes use of an electron beam scanning system configured to generate a plurality of electron beam scans over substantially an entire sample, with each scan varying in electron-illumination intensity over the course of the scan. A set of sampling measurements, captured using a number, M, of such spatial electron-illumination intensity masks (where M<N) is used to reconstruct the image (or diffraction pattern, EELS, or EDX, etc.) that would have been produced had the measurement encompassed collecting data over the entire array of N spatial pixels for the full duration of the data acquisition period. As mentioned above, any of a number of mathematical reconstruction techniques can be used to solve the underdetermined system of linear equations arising from the set of sampling measurements to produce an accurate reconstruction of the original, full resolution image. Under favorable circumstances, such a system can be expected to acquire essentially the same information as a conventional TEM or SEM system, but with potentially much faster data acquisition times and much smaller data storage and handling requirements. The method was intended primarily for use in spatially-resolved diffraction and spectroscopy measurements performed in a TEM, but the potential application space is much larger than this.

Time Domain-Encoded Temporal Compressive Sensing:

Disclosed herein is an alternative approach to the temporal compressive sensing method described above (i.e., temporal compressive sensing in which the test functions are encoded in the time domain as opposed to the spatial domain) that is potentially applicable to a wide variety of signal acquisition and processing fields in addition to optical video and electron microscopy. In addition, several distinct hardware implementations of the approach are disclosed that enable operation in very different time domains (e.g., ranging from microsecond-scale to picosecond-scale time resolution).

To describe the new approach and distinguish it from previous work, we start by describing the existing approach of coded-aperture video compressive sensing (i.e., spatially-encoded video compressive sensing) in more detail. In very general terms, coded-aperture video compressive sensing works by spatially-encoding multiple reconstructible frames of video data into a single acquired video frame. We will describe an example using typical values for operational parameters, with the understanding that the actual range of operational parameters in practice can be quite large. An acquired video frame may, for example, be a single frame acquired by a charge-coupled device (CCD) camera operating in continuous acquisition mode at 100 Hz, so that each frame represents an acquisition time of somewhat less than 10 milliseconds (after accounting for data read-out overhead). Throughout, we will refer to this 10-millisecond span, which is the exposure time of a conventional acquisition system such as a camera, as a "block of time". Thus, with a standard video acquisition system, one acquires one and only one frame per block of time.

Now consider how the coded-aperture video compression system works. Suppose that the CCD camera has a 1024×1024 array of pixels. At any given instant within a 10 ms block of time, a coded aperture blocks or attenuates the signal reaching some fraction of the CCD pixels. This coded aperture is capable of being physically moved very rapidly in a known trajectory, so that it can be moved to 100 or more significantly distinct locations during the 10 ms exposure time. Conceptually, we can break up the 10 ms exposure time into 100 distinct "time slices", each of which is 0.1 ms long. The intent is to determine what image was striking the full set of 1024×1024 pixels in each one of those 100 time slices, or in other words, to calculate 100 reconstructed frames from the single 1024×1024-pixel acquisition. This is possible for two reasons. First, each pixel is recording the total intensity from a certain known linear combination of the 100 time slices, and the coefficients governing this linear combination are different for different pixels. Therefore each pixel represents information from a different subset (or, more generally, weighted average) of the time slices, and this means that there is information in the acquired image that in some respect distinguishes the 100 time slices from one another. Second, real-world video data generally has a high degree of information redundancy, so that the actual number of independent data points required to describe, for example, a 1024 pixel×1024 pixel×100 frame video is much less than the ~$10^8$ value one might expect from a simple count of space-time voxels. Depending on the speed and degree of complexity of the motion in the video, and the amount of distortion acceptable for a given application, data compression ratios of 10:1 or 100:1 or even greater may be possible. There are multiple published examples of coded-aperture optical video compressive sensing that achieve compression rates of 100:1 or more, with moderate yet acceptable levels of distortion. This distortion is considered to be a small price to pay for effectively multiplying the frame rate (i.e., the data acquisition and read-out rate) of an inexpensive camera by a factor of 100 or more (i.e., the effective data acquisition and read-out rate, and thus the time resolution, of the camera exceeds that determined by its hardware limits).

This example illustrates the reconstruction of 100 "time slice" video frames of 0.1 ms duration, each with 1024×1024 pixels, from a single 10 ms acquired video frame of 1024×1024 pixels. Each pixel in the acquired frame represents a different linear combination of information (as determined by the series of spatial masks used during acquisition) from the same spatial location in the 100 different time slices, and we acquire one frame per 10 ms block of time. In mathematical terms, this can be expressed as:

$$M_{ij} = \Sigma_k c_{ijk} V_{ijk} + \text{noise}, \quad (2)$$

where $M_{ij}$ are the measured video frames (comprising the complete set of pixel data, such that indices i and j represent rows and columns in the image, respectively), $V_{ijk}$ are the video frames to be reconstructed (i.e., the set of N time slice frames), and $c_{ijk}$ are the set of coefficients describing the manner in which the illumination that would normally reach each pixel is blocked and/or attenuated at a given point in time. The noise term, while important to the theory and application of compressive sensing, has well understood implications and need not concern us for purposes of the present discussion. In some implementations the spatial masking pattern is binary, such that each $c_{ij}$ value is either 0 or 1, but this is not a necessary constraint. In our example, k ranges from 1 to 100, and i and j each range from 1 to 1024. The objective of the mathematical reconstruction, then, is to produce an estimate of $V_{ijk}$ when $M_{ij}$ and $c_{ijk}$ are known, using for example sparsity in some particular mathematical representation to constrain the underdetermined system of linear equations. Methods for determining such mathematical representations and algorithms for performing the reconstruction are well covered by the (extensive) compressive sensing literature (see for example, Duarte et al. (2008) "Single-Pixel Imaging via Compressive Sampling", IEEE Signal Processing Magazine, March 2008, pages 83-91; Stevens et al., (2015), "Applying Compressive Sensing to TEM Video: a Substantial Frame Rate Increase on any Camera", Adv. Structural and Chemical Imaging 1:10). The process is repeated for each image $M_{ij}$ returned by the camera, with one $M_{ij}$ recorded per block of time. The reconstruction algorithm can operate on a single $M_{ij}$ at a time, or can operate on multiple $M_{ij}$ simultaneously in order to take advantage of continuity from one set of 100 reconstructed frames to the next. Note that, throughout this discussion, the actual physical interpretation of indices i and j will depend upon the measurement system and its operating mode. In general, they represent the rows and columns of a camera, regardless of how that camera is being used. In some cases the camera will be a linear array and not a two-dimensional array, and in all such cases the pair ij of indices should be considered to be replaced by a single index i. In the case of real-space imaging, the i and j indices will be linearly related to the Cartesian coordinates in the plane of the sample or scene under study. In the case of diffraction patterns, the i and j indices will typically represent, to a linear approximation, the two-dimensional scattering angle induced in the probe particles by the sample under study. In the case of spectroscopy, one of these two indices will represent a spectral coordinate (such as energy loss, wavelength shift, or x-ray photon energy) and the other index, if it exists, may or may not have a simple physical interpretation depending on the physical operation principles of the spectroscopy system. For example, in electron energy-loss spectroscopy this other index typically represents one of the spatial coordinates in the sample plane, one of the components of scattering angle, or a linear combination of these.

Figure 2:
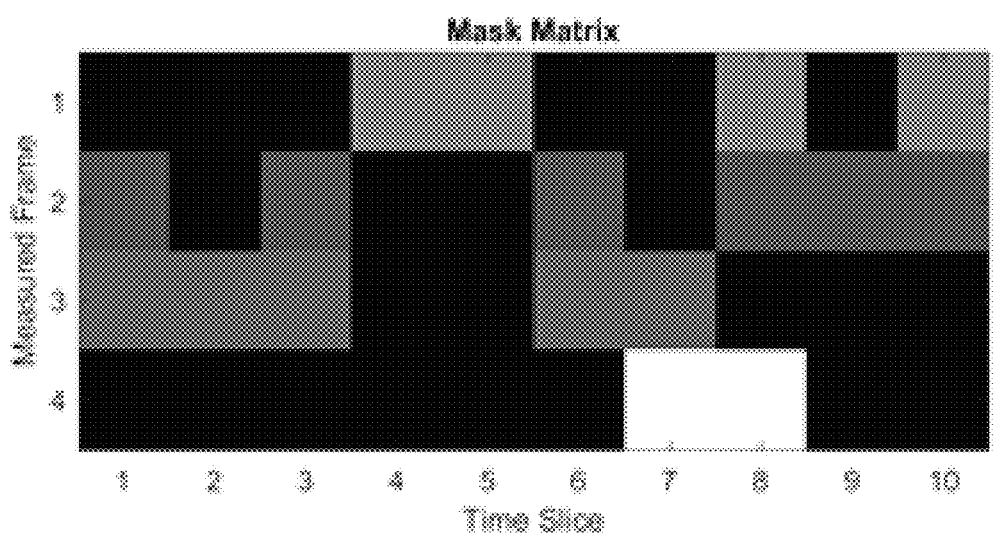
FIG. 2 illustrates different combinations of ten time slice datasets that are sent to four different regions of a large camera using a fast switching system, and digitally segmented into four image frames (i.e., a 2×2 array of images captured by the large camera sensor) for analysis. The mask matrix, also called the measurement matrix, is in this case a 4×10 array of real numbers specifying the coefficients expressing each of the four measured frames as a linear combination of the image data from ten distinct time slices.

The approach to time domain-encoded temporal video compressive sensing disclosed herein (which can be applicable to more than just video compressive sensing as it may be applied to other types of data, for example, spectroscopic results that vary rapidly as a function of time) is mathematically distinct from the spatially-encoded method described above. Rather than capture a single image with different spatially-dependent coefficients that vary in time for each image pixel (or spectroscopy channel, for spectroscopic information), we propose to capture multiple full resolution images (or, more generally, data sets) per block of acquisition time, each of which is a distinct linear combination of images from different time slices. Mathematically, this is represented as:

$$M_{ijl} = \Sigma_k c_{lk} V_{ijk} + \text{noise}, \quad (3)$$

where we have added an additional index l to distinguish different images (or measurement data sets) acquired during the same data acquisition period (i.e., the same block of time). Note that the coefficients $c_{lk}$ are now independent of spatial pixel (i, j). This set $c_{lk}$ of coefficients plays the role of the measurement matrix or mask matrix Φ, as illustrated for example in FIG. 2.

In one implementation, equation (3) can be interpreted as asserting that we have multiple cameras (each with 1024×1024 pixels, for example) and a system for projecting a different linear combination of time slice images onto each such camera, such that it effectively multiplies the camera speed. The system should be fast enough to switch states many times per reconstructed time slice, so that different linear combinations of each time slice can be sent to each camera. These need not be physically distinct cameras. They could, for example, be 16 distinct regions on a 4096×4096 pixel camera with, for example, a fast-switching mirror array (for optical systems) or a high-speed deflector system (for electron-optical systems) acting as the switching system. If the switching system is extremely fast, then the transients (e.g., blur during the settling time of an electrostatic deflector) may be negligible on the timescale relevant to the operator. In other cases, it would be advantageous to couple the system with a second high-speed switching system (e.g., a beam blanker in an electron microscope) that prevents signal from reaching the detector during this transient time. The switching could also be done with an array of variable beam-splitting systems that can each send some fraction of signal to each of two different paths, using for example electro-optical modulators. In another implementation, the multiple "cameras" could be multiple sets of local capacitive bins for storage of intensity information in a large and complex complementary metal oxide semiconductor (CMOS) detector array, with a high-speed clock/multiplexer system for deciding which set of bins is to be filled at any given point in time. In all of these cases "fast" and "high-speed" are relative to the duration of a time slice, such that the system must be able to switch states multiple times per time slice. Or, if the sequence of events represented by the video $V_{ijk}$ is precisely reproducible, each index could represent a separate run of this sequence of events with a different temporal masking pattern $c_{jk}$ for each, for example by rapidly modulating the electron beam current as a function of time in an electron microscope during each acquisition. All of these potential physical embodiments represent different implementations of the same mathematical model represented in equation (3). Note that in many embodiments of the disclosed temporal compressive sensing method, the temporal switching may be accomplished either through the design of the illumination system (to enable rapidly varying illumination intensities) or through the design of the detection system (using multiple sensors or a rapid switching system as described above) while still realizing the same concept described by the mathematical model.

As used throughout this disclosure, the terms "rapid", "rapidly", "fast" and "high-speed" are used to characterize the timescale on which specified process steps occur relative to the duration of a data acquisition period (e.g. the exposure time for an image sensor). For example, a "rapid" switching process may be one in which the system is capable of switching at least 2 times, at least 4 times, at least 6 times, at least 8 times, at least 10 times, at least 25 times, at least 50 times, at least 75 times, at least 100 times, or more, between different system states (e.g. states corresponding to different illumination intensities) during the course of a single data acquisition period (e.g., the exposure interval or data acquisition period used to capture an image with an image sensor).

In many embodiments, the number of time slices is not dictated by the physical measurement system itself and can be adjusted after the fact during the computational analysis of the data to allow the effective frame rate to be adapted to the data. The compressibility and signal-to-noise ratio of the data stream may not be known in advance, and may indeed vary with time for a single series of acquisitions. The computer software that performs the reconstruction will know exactly which detector(s) or detector region(s) were receiving signal at every single point in time during each acquisition and, therefore, the computer may calculate a range of measurement matrices, each with a different number of time slices. In a non-adaptive system, these calculations could be performed before any measurements are acquired, thus saving computation time during the acquisition. Based on any of a number of readily available mathematical metrics (e.g. the calculated reconstruction uncertainty in a Bayesian model), the software could choose the number of time slices for each acquisition in such a way as to produce a specified level of reconstruction fidelity while still providing the highest effective time resolution possible. In the limit of extremely low compressibility of the data stream, such a system may at times use a number of time slices equal to the number of detectors (or detector regions). This will always be possible provided one defines the acquisition sequence so that the square measurement matrix produced in this case is sufficiently well-conditioned, allowing numerically stable calculation of the no-longer-underdetermined set of linear equations. Such adaptive reconstruction techniques are not necessarily possible, or not necessarily as effective or practical or easy to calculate, in the case of compressive sensing based on spatial modulation, which requires significant computation to be performed before the reconstruction produces even a recognizable image, and in the case of extremely poor signal-to-noise ratio and excessive compression, may never produce a recognizable image at all.

Computer simulations (e.g., see Example 1) demonstrate that a time domain-encoded temporal compressive sensing system based on equation (3) can provide reconstruction of video data with the number of time slices significantly exceeding the number of measurements (i.e., the number of distinct values of the index 1), using algorithms similar to those described in the technical literature (e.g., $l_1$-norm regularization, total-variation (TV) regularization, and dictionary learning (Bayesian or otherwise)). These results establish the mathematical validity of the concept, and place it in a position to take advantage of continued advances in compressive sensing algorithms.

Temporally Multiplexed Compressive Sensing:

A more general model, which we will call temporally multiplexed compressive sensing (TMCS), can be constructed that includes equations (2) and (3) as special cases:

$$M_{ijl} = \Sigma_k c_{ijkl} V_{ijk} + \text{noise}, \quad (4)$$

which can be interpreted in two different ways. We can describe this as multiple simultaneous (or effectively simultaneous, if we have a switching system that can change states many times within a single time slice) measurements of the type described by equation (2) or as a measurement of the type described by equation (3) but with the additional flexibility afforded by allowing the $c_{ijkl}$ coefficients to vary as a function of position as well as time. Implementing this in the multiple-capacitive-bin CMOS concept, or in a system based on the use of a micromirror array, may be quite feasible. The concept described in United States Patent Application 2015/0153227A1 implements equation (3) in the limited case of only two distinct values of the index 1, as it describes two coded-aperture video systems operating in parallel, thus potentially overcoming some of the mathematical difficulties of video reconstruction when the measured data are limited to a single coded aperture. This is entirely distinct from the concepts of the present disclosure. The concept in U.S. 2015/0153227 A1 still achieves video compression using the essential modality of other coded-aperture video systems, and it only uses the redundant measurement to improve the mathematical properties of the reconstruction. US20150153227 A1 does not recognize that, when the number of simultaneously acquired data sets (e.g., full-resolution images) exceeds 2, an entirely different modality of temporal compression becomes available, as described in the present disclosure. The methods and systems of the present disclosure can operate in the mode described by equation (3), but in many embodiments they are not necessarily limited to this mode, for example they can operate in a mode described by the more general equation (4). The methods and systems of U.S. 2015/0153227 A1 cannot effectively operate in the mode described by equation (3), for they would be limited to a very small number M=2 of measurements, and sparsity-based reconstruction methods perform poorly, if at all, for such a small number of measurements. Further, the compressive sensing scheme disclosed in U.S. 2015/0153227 A1, like all coded-aperture video compression schemes, requires significant computational resources to produce a reconstructed video of acceptable quality. This is because the compression scheme employed depends on a complicated scheme of spatiotemporal modulation, and coded-aperture schemes only directly capture one (in most cases) or two (in the case of U.S. 2015/0153227 A1) actual real-space images during a single block of time. The scheme of the present invention, in contrast, captures multiple full-resolution data sets (e.g., images) in each block of time, and even an elementary pseudoinverse calculation (which requires a negligible fraction of one second) suffices to provide a first-approximation reconstruction that clearly resembles the final result well enough for a human user to evaluate the quality of the acquisition in real time. Finally, in many embodiments, the presently disclosed methods and systems can direct virtually all of the photons (in an optical system) or electrons (in an electron microscope) to the various detectors or detector regions, without significant waste. By contrast, coded-aperture schemes by their very nature block substantial fractions of the signal (typically ~50%).

This concept can be generalized yet further into a model:

$$M_{ijl} = \Sigma_{i'j'k} c_{iji'j'kl} V_{i'j'k} + \text{noise}, \quad (5)$$

where the intent is that the index i has the same range as the index i' and the index j has the same range as the index j'. This equation indicates that the measurement $M_{ijl}$ consists of multiple measurements of images of the same size and shape as the images to be reconstructed, but that the coefficients can now mix information from different parts of the image, for example in order to implement such things as convolution filters (so that the compressive sensing reconstruction process also performs a de-blurring enhancement or an edge-enhancement or some other feature enhancement, for example based on learned or optimized dictionaries) or complex coding schemes that take advantage of the typical patterns of spatiotemporal correlation in a video to minimize redundancy in the extraction of information from the system being measured.

Finally, we can remove the constraints on the indices i and j in equation (5) and produce a model in which the measurement is just a general linear operator acting on the video (or sensor) data, plus a noise term. If we further eliminate the concept of "blocks of time" so that (for example) the system operates in a rolling-acquisition mode without well-defined non-overlapping blocks of time slices, and if we allow the time slices themselves to vary in duration and even to partially overlap, then the model becomes quite general indeed.

With each generalization of the fundamental model, there is the potential for improving the performance of the compressive sensing reconstruction system, including adding new capabilities such as de-blurring. Generalizing the model certainly cannot make the performance worse, since by the very nature of generalization each specific model is a strict subset of the more general one. This generalization comes at the cost of complexity (both in the physical acquisition system required and in the reconstruction algorithm used) and, potentially, the computational resources required for the reconstruction. The real-world value and practicality of implementing the generalized conceptual models described by equations (4) and (5) can be assessed through numerical simulations. It is already known from numerical simulation that equations (2) and (3) can each form the basis of an effective time domain-encoded compressive sensing system that can be used to reconstruct significantly more frames of video data (or, more generally, time-dependent data sets) than are directly measured. There is published work on video compressive sensing using spatial-multiplexing cameras (SMCs) based, for example, on a single-pixel camera (see, for example, Duarte et al., "Single-Pixel Imaging Via Compressive Sampling", IEEE Signal Processing Magazine, March, 2008, page 83-92), but this is approach is mathematically distinct from the TMCS approach disclosed herein which directly captures multiple images per block of time with no need for complex encoding or reconstruction of the spatial information.

The compressive sensing system concept disclosed herein is that of a system that acquires not just one but multiple images (or data sets) from a single block of data acquisition time, with each image or data set representing a different linear combination of time slices within that block of time. These multiple images or data sets comprise intensity data acquired using a system that either simultaneously sends signal to multiple detectors (e.g., an optical beam splitter array with rapid switching achieved using an electro-optical modulator), or that selects which detector is to receive the signal at any given instant in time using a switching system (e.g., a set of deflector plates for an electron microscope) that can switch multiple times per time slice.

Advantages of Temporally Multiplexed Compressive Sensing:

In addition to overcoming the disadvantages of coded-aperture video compressive sensing that are specific to electron microscope applications, as discussed above, TMCS may overcome blurring artifacts associated with optical coded-aperture compressive sensing. Coded-aperture compressive sensing can produce noticeable blurring artifacts aligned with the direction of motion of the aperture. While these artifacts are sometimes negligible, there are cases (e.g., in videos of complex scenes in which there are many objects in motion at speeds comparable to one pixel per time slice, or greater) in which the artifacts are quite obvious. Because the TMCS approach does not inherently involve any "scrambling" of the spatial information or any preferred direction in image space, this particular source of reconstruction distortion does not exist in TMCS.

In addition, TMCS produces directly interpretable images even before any reconstruction is applied. Further, unlike a coded-aperture system, a TMCS system can be operated in a mode that produces high-time-resolution videos directly, by operating in a direct acquisition mode rather than a compressive-sensing mode. For example, if we have a system that captures 16 images per block of time, with an arbitrary (up to the physical limits of the switching system) coefficient matrix $c_{ik}$ (as described in Equation (3)), we can, if we wish, specify that some or all of the 16 images do not mix information from widely separated points in time, but rather collect data from a contiguous small number (perhaps only one) of the time slices. In this case the exposure time for each of the 16 images can be extremely short, limited by the speed of the switching system, provided the available illumination intensity is high enough to produce an image of adequate signal-to-noise ratio in such a short time. Thus the TMCS system could be operated so that some, or even all, of the measured images represent snapshots with extremely low exposure times, even much shorter than the time slices used in a typical compressive sensing mode. The price of this operation mode, if taken to its limit, is that the duty cycle of the exposure may be extremely low, so that little or no information is available from some, perhaps most, of the time slices. For some applications (e.g., experiments in which a sequence of events is triggered and thus will come at some precisely known span of time), this may provide extremely high time resolution that is difficult to obtain through other approaches, thus entering an application space overlapping with that of Movie Mode Dynamic Transmission Electron Microscopy (previously described in U.S. Pat. No. 9,165,743).

The simpler mathematical form of the governing equation for TMCS (equation (3)) as opposed to coded-aperture video compressive sensing (equation (2)) can have advantages in terms of the computational resources required for reconstruction. Because the spatial information is represented directly in TMCS, a rough-draft reconstruction can be produced extremely quickly by any of a number of simple algorithms (e.g., placing each acquired image into the span of time slices in which its coefficients are greater than the coefficients of any other acquired image), and iterative algorithms can incrementally improve that estimate both online (i.e., during the ongoing acquisition) and offline (i.e., later on, possibly with a much larger computer). Many other compressive sensing systems provide a compressed data stream that cannot be directly interpreted, and must go through significant processing before recognizable results appear, and this can be a significant problem for practical implementation, since the user sometimes cannot see whether the data is useable until long after the experiment is over.

Provided the switching-time overhead is small (i.e., only a small fraction of the time is spent switching from one set of output channels to another), the effective duty cycle of TMCS (i.e., the fraction of total available signal that the system acquires) can be very close to 1. Typically, coded-aperture compressive sensing has a duty cycle of approximately one half, since roughly half of the pixels are blocked at any given instant in time. This means TMCS can potentially make better use of available signal, by nearly a factor of 2.

Applications:

The time domain-encoded temporal compressive sensing methods disclosed herein may be adopted in a variety of imaging and spectroscopy applications including, but not limited to, optical video imaging, time-resolved optical spectroscopy, and transmission electron microscopy (e.g., for capture of image data, diffraction pattern data, electron energy-loss spectra, energy-dispersive X-ray spectra, etc.). Furthermore, the temporal compressive sensing methods disclosed herein may be used to capture signals (i.e., images, spectra, diffraction patterns, etc.) arising through the interaction of radiation with a sample or scene such that the radiation is transmitted, reflected, elastically scattered, or in-elastically scattered by the sample or scene, thereby forming patterns of transmitted, reflected, elastically scattered, or inelastically scattered radiation which are detected using one- or two-dimensional sensor arrays. Depending on the application, the radiation may be electro-magnetic radiation, particle radiation, or any combination thereof. Suitable radiation sources include, but are not limited to, electromagnetic radiation sources, electron guns, ion sources, particle accelerators, and the like, or any combination thereof.

The time domain-encoded temporal compressive sensing methods disclosed herein may be directly applied to the study of the evolution of events and physical processes in time. However, its range of application goes well beyond this, because there are numerous applications in which another coordinate of interest may, in effect, be mapped to the time axis by the manner in which the system works. One such example is tomography, in which a sample under study is rotated and a series of measurements is acquired over a range of rotation angles. Rotating the sample implies a varying sample orientation as a function of time, i.e., a mapping (not necessarily one-to-one) between orientation and time. In cases such that the ability to capture tomographic data is limited by the measurement rate of a camera, temporal compression could substantially accelerate data acquisition upon increasing the rate of sample rotation to take advantage of the increased effective frame rate of the camera. Similarly, scanning transmission electron microscopy (STEM) operates by scanning a focused electron beam across a region of a sample (i.e., in which the electron beam diameter is narrow relative to the cross-sectional area of the sample to be analyzed or imaged) and capturing a data set (be it a high-angle annular dark field (HAADF) signal, an electron energy-loss spectrum (EELS), an energy-dispersive x-ray spectrum (EDX), a bright-field signal, a diffraction pattern, or a combination of these) at every scan position. The act of scanning creates a mathematical map between position and time and, just as in the tomography example, if the system limitation is in the camera speed (as it very often is, for example, in STEM-diffraction), then temporal compression has the potential to greatly improve data throughput. This embodiment would have similar capabilities as the methods and systems disclosed in U.S. Pat. No. 9,165,743, but it operates on a completely different principle. Specifically, the presently disclosed methods achieve compressive sensing primarily through temporal modulation (in this case, by varying the position on the sample of the focused electron probe as a function of time) and, while they may take advantage of spatial modulation, they are not necessarily dependent on spatial modulation. All previous applications of compressive sensing in electron microscopy, both proposed and actually implemented, necessarily rely on either spatial modulation or simple under-sampling and in-painting to achieve compression, and fail to describe the mechanism of temporal compression described in the present disclosure. As illustrated in the tomography and scanning transmission electron microscopy (STEM) examples discussed above, in some embodiments of the disclosed temporal compressive sensing methods and systems, distinct linear combinations of patterns of the radiation transmitted, reflected, elastically scattered, or in-elastically scattered by a sample (or a scene) for a series of time slices may be generated by modulating an experimental parameter other than the radiation intensity itself in a temporal fashion. For example, in some embodiments, the experimental parameter to be temporally modulated may be selected from the group consisting of rotational orientation of the sample, linear translation and/or tilt of the electron probe in one dimension, linear translation and/or tilt of the electron probe in two dimensions, linear translation of the sample in one dimension, linear translation of the sample in two dimensions, and linear translation of the sample in three dimensions, or any combination thereof. In some embodiments, the radiation incident on the sample (or scene) is focused to a narrow beam (i.e., having a beam diameter that is small relative to the cross-sectional area of the sample or scene to be imaged or analyzed) and the experimental parameter to be temporally modulated is the position of the beam relative to the sample (or vice versa).

Optical Imaging & Spectroscopy Systems:

Optical imaging and spectroscopy systems based on the disclosed time domain-encoded temporal compressive sensing may be developed for a variety of applications using a variety of commercially-available optical system components, e.g., light sources, optical modulators, and sensors, as well as other active or passive components such as lenses, mirrors, prisms, beam-splitters, optical amplifiers, optical fibers, optical filters, monochromators, etc. Examples of optical imaging applications include, but are not limited to, video imaging, visible light imaging, infrared imaging, ultraviolet imaging, fluorescence imaging, Raman imaging, and the like. Example of spectroscopy applications include, but are not limited to, absorbance measurements, transmittance measurements, reflectance measurements, fluorescence measurements, Raman scattering measurements, and the like.

Light sources for use in temporal compressive sensing systems of the present disclosure may include, but are not limited to, incandescent lights, tungsten-halogen lights, light-emitting diodes (LEDs), arc lamps, diode lasers, and lasers, or any other source of electromagnetic radiation, including ultraviolet (UV), visible, and infrared (IR) radiation. In some applications, natural light arising from solar radiation (i.e., produced by the sun), may serve to illuminate a sample or scene for which temporally compressed data is acquired.

High speed switching of optical signals may be achieved through any of a variety of approaches including, but not limited to, the use of optical modulators, e.g., electro-optic modulators or acousto-optic modulators, or digital micro-mirror array devices. In some embodiments of the disclosed compressive sensing methods and systems, the switching times achieved may range from less than 1 nanosecond to about 10 milliseconds. In some embodiments, the switching times may be at least or at least about 1 nanosecond, at least or at least about 10 nanoseconds, at least or at least about 100 nanoseconds, at least or at least about 1 microsecond, at least or at least about 10 microseconds, at least or at least about 100 microseconds, at least or at least about 1 millisecond, or at least or at least about 10 milliseconds. In some embodiments, the switching times achieved may be at most or at most about 10 milliseconds, at most or at most about 1 millisecond, at most or at most about 100 microseconds, at most or at most about 10 microseconds, at most or at most about 1 microsecond, at most or at most about 100 nanoseconds, at most or at most about 10 nanoseconds, or at most or at most about 1 nanosecond. Those of skill in the art will recognize that the switching times that are achievable may have any value within this range, e.g. about 500 nanoseconds.

Examples of suitable sensors, sensor arrays, or detectors for use in the temporal compressive sensing methods of the present disclosure include, but are not limited to, photo-diodes, avalanche photodiodes, photodiode arrays, photomultipliers, photomultiplier arrays, charge coupled devices (CCDs), image intensified CCDs, and complementary metal oxide semiconductor (CMOS) sensors, CMOS framing cameras (e.g., CMOS cameras that can store multiple images or datasets on-chip through the use of multiple capacitive bins at each pixel and an electronic switching system that determines which set of bins is accumulating signal at any given time), or any combination thereof. In some embodiments, the sensors, sensor arrays, or detectors for use in the temporal compressive sensing methods of the present disclosure may further comprise a nonlinear optical material, a fluorescent material, a phosphorescent material, or a microchannel plate, that converts or amplifies the radiation provided by the radiation source into a form of radiation that is directly detectable by the sensor, sensor array, or detector. For purposes of the present disclosure, the term "sensor array" and its grammatical equivalents is meant to include "point" arrays (e.g., single pixel sensors) as well as one-dimensional (linear) arrays, two-dimensional arrays, and so forth. Furthermore, the term "detector" and its grammatical equivalents is meant to include the individual sensors and sensor arrays, as described above, as well as combinations of optical components and sensors, for example, spectrometers comprising a monochromator optically coupled with a photodiode array or CCD camera. Suitable linear or two-dimensional sensor arrays may comprise a wide variety of individual pixels.

Sensor arrays suitable for use in the disclosed temporal compressive sensing systems may comprise from or from about 2 to $100 \times 10^6$ pixels, or more. In some embodiments, sensor arrays for use in the disclosed temporal compressive sensing systems may comprise at least or at least about 2 pixels, at least or at least about 10 pixels, at least or at least about 100 pixels, at least or at least about 1,000 pixels, at least or at least about 10,000 pixels, at least or at least about 100,000 pixels, at least or at least about 1,000,000 pixels, at least or at least about $10 \times 10^6$ pixels, at least or at least about $100 \times 10^6$ pixels, or more. In some embodiments, sensor arrays for use in the disclosed temporal compressive sensing systems may comprise at most or at most about $100 \times 10^6$ pixels, at most or at most about $10 \times 10^6$ pixels, at most or at most about 1,000,000 pixels, at most or at most about 100,000 pixels, at most or at most about 10,000 pixels, at most or at most about 1,000 pixels, at most or at most about 100 pixels, at most or at most about 10 pixels, or at most or at most about 2 pixels. One of skill in the art will recognize that the total number of pixels in the sensor array may include any value within this range, for example, about $12 \times 10^6$ pixels.

The term "about" and its grammatical equivalents, in relation to a reference numerical value can include a range of values plus or minus 10% from that value. For example the amount "about 10" can include amounts from 9 to 11. The term "about" in relation to a reference numerical value can also include a range of values plus or minus 10%, 9%, 8%, 7%, 6%, 5%, 4%, 3%, 2%, or 1% from that value.

Sensor arrays suitable for use in the disclosed temporal compressive sensing systems may comprise pixels of size ranging from or from about 0.1 µm to or to about 20 µm on a side. In some embodiments, sensor arrays for use in the disclosed temporal compressive sensing systems may comprise pixels of at least or at least about 0.1 µm, at least or at least about 0.25 µm, at least or at least about 0.5 µm, at least or at least about 0.75 µm, at least or at least about 1 µm, at least or at least about 2.5 µm, at least or at least about 5 µm, at least or at least about 7.5 µm, at least or at least about 10

μm, at least or at least about 15 μm, or at least or at least about 20 μm, or larger. In some embodiments, sensor arrays for use in the disclosed systems may comprise pixels of at most or at most about 20 μm, at most or at most about 15 μm, at most or at most about 10 μm, at most or at most about 7.5 μm, at most or at most about 5 μm, at most or at most about 2.5 μm, at most or at most about 1 μm, at most or at most about 0.75 μm, at most or at most about 0.5 μm, at most or at most about 0.25 μm, or at most or at most about 0.1 μm on a side, or smaller. One of skill in the art will recognize that the pixels in the sensor array may have any value within this range, for example, about or at most about 0.8 μm on side.

Sensor arrays suitable for use in the temporal compressive sensing systems of the present disclosure may operate at data acquisition and read-out rates ranging from or from about 0.001 frames/sec (or lower) to or to about 100,000 frames/sec (or higher). In some embodiments, sensor arrays suitable for use in the disclosed temporal compressive sensing systems may operate at data acquisition and read-out rates of at least or at least about 0.001 frames/sec, at least or at least about 0.01 frames/sec, at least or at least about 0.1 frames/sec, at least or at least about 1 frame/sec, at least or at least about 10 frames/sec, at least or at least about 100 frames/sec, at least or at least about 1,000 frames/sec, at least or at least about 10,000 frames/sec, at least or at least about 100,000 frames/sec, or higher. In some embodiments, sensor arrays suitable for use in the disclosed temporal compressive sensing systems may operate at data acquisition and read-out rates of at most or at most about 100,000 frames/sec, at most or at most about 10,000 frames/sec, at most or at most about 1,000 frames/sec, at most or at most about 100 frames/sec, at most or at most about 10 frames/sec, at most or at most about 1 frame/sec, at most or at most about 0.1 frames/sec, at most or at most about 0.01 frames/sec, or at most or at most about 0.001 frames/sec, or lower. One of skill in the art will recognize that the sensor array may operate at a data acquisition and read-out rate having any value within this range, for example, about 60 frames/sec.

For temporal compressive sensing systems in which high speed switching components are used to deflect images or other datasets to one of several different regions (or "sub-regions", "sub-units", etc.) of a two-dimensional sensor array, the total number of available regions may comprise either a linear array or a two dimensional array comprising anywhere from 2 to 400 or more individual regions. For two dimensional sensor arrays in which the pattern of regions is organized as a square N×N array, the array of regions may comprise a 2×2 array, a 3×3 array, a 4×4 array, a 5×5 array, a 6×6 array, a 7×7 array, an 8×8 array, a 9×9 array, a 10×10 array, an 11×11 array, a 12×12 array, a 13×13 array, a 14×14 array, a 15×15 array, a 16×16 array, a 17×17 array, an 18×18 array, a 19×19 array, or a 20×20 array, or a higher dimension N×N array. In some embodiments, the pattern of regions may be organized as a rectangular array (e.g., an M×N array) comprising a 2×3, array, a 2×4 array, a 2×5 array, a 2×6 array, a 3×2 array, a 3×4 array, a 3×5 array, a 3×6 array, a 4×2 array, a 4×3 array, a 4×5 array, a 4×6 array, a 5×2 array, a 5×3 array, a 5×4 array, a 5×6 array, a 6×2 array, a 6×3 array, a 6×4 array, a 6×5 array, or a higher order M×N array. In some embodiments, the pattern of regions may comprise a hexagonal array, a parallelogram array, an irregular array, a randomly distributed array, or any combination thereof, with or without missing elements. Each region may have no overlap with other regions, or some regions may have partial or full overlap with some regions, or some regions may be subsets of other regions. Each region may be a circular region, an elliptical region, a square region, a rectangular region, a hexagonal region, a regular polygonal region, an irregular polygonal region, a region of any shape comprising a simply-connected subset of pixels, or a region of any shape comprising a non-simply-connected subset of pixels. Each region may be identical in size and shape to all other regions, or some regions may differ in size from other regions, or some regions may differ in shape from other regions, or some regions may differ in both size and shape from other regions. Each region may be identical in orientation to other regions, or some regions may have orientations rotated with respect to the orientations of other regions, or some regions may have orientations reflected with respect to the orientations of other regions, or some regions may have orientations that are both rotated and reflected with respect to the orientations of other regions. Each region may be identical in scale or magnification to other regions, or some regions may differ in scale or magnification in one coordinate axis with respect to other regions, or some regions may differ in scale or magnification in two coordinate axes with respect to other regions. In the case in which one or both coordinates in the camera plane may be identified with real-space coordinates in a sample plane or a scene, each region may record the same region of such real-space coordinates as other regions, or the regions it records may partially overlap with, or be a strict subset of, or be a strict superset of, one or more other such regions. In the case in which one or both coordinates in the camera plane may be identified with a linear approximation of scattering angles, each region may record the same set of scattering angles as other regions, or the regions it records may partially overlap with, or be a strict subset of, or be a strict superset of, one or more other such sets of scattering angles. In the case in which one or both coordinates in the camera plane may be identified with a spectral coordinate, including but not limited to energy loss, wavelength shift, or photon energy, each region may record the same region of such spectral coordinates as other regions, or the regions it records may partially overlap with, or be a strict subset of, or be a strict superset of, one or more other such regions of spectral coordinates.

Electron Microscopy & Spectroscopy Systems:

Electron microscopy systems for implementing the temporal compressive sensing methods disclosed herein may comprise a variety of system components including, but not limited to, electron beam sources, electron beam shutters ("beam blankers" or "beam blanking systems"), electron focusing optics, sample holders that incorporate various sample stimulus devices, electron deflector systems, and image sensors or other data capture devices.

Suitable electron beam sources may include, but are not limited to, electron guns (electron emitters) based on thermionic, photocathode, laser-driven photocathode, cold emission, or plasma source emission mechanisms that emit either continuous or pulsed streams of electrons. An exemplary system for generating precisely-controlled series of electron pulses is based on the use of an arbitrary waveform generator (AWG) laser system and photocathode, as described in U.S. Pat. No. 9,165,743. Electron beam focusing may be achieved in these systems through purely electrostatic approaches and/or may utilize magnetic fields.

In some embodiments, the electron microscope system may incorporate a sample holder and a sample stimulus mechanism, e.g., a pulsed sample drive laser that provides highly precise, adjustable, and intense heat for initiating dynamic processes in the sample under study. Other methods of initiating processes in the sample may also be employed, e.g., through electrically triggered sample holders, or external electronics connected to sample holders that may deliver a voltage pulse, a current pulse, an electrically-driven heat pulse, or an impulse delivered to the sample with the aid of a nano-indentation device or micro- or nano-electromechanical system.

In some embodiments, the electron microscope system may incorporate accurately-timed, high-speed electron deflector systems, including electrostatic deflector systems and/or magnetic deflector systems. An exemplary electrostatic deflector system is described in U.S. Pat. No. 9,165,743. One embodiment of an electrostatic deflector system disclosed therein includes four high voltage switches connected to customized deflector plates which are inserted into the lower part of the projector lens (e.g., the last electromagnetic lens in a standard TEM) below the sample. The two pairs of orthogonally positioned deflector plates deflect each image (or diffraction pattern, etc.) arising through interaction of electrons with the sample to a different part of the camera, thereby overcoming a typical camera's multi-second refresh rate. Each of the four plates may independently carry a voltage ranging from or from about, for example, −800V to +800V, thereby allowing complete flexibility over the electron deflection in two dimensions. The camera itself is typically positioned at or at about 50 cm below this set of deflectors, so that the electron beam can be directed to any part of the camera (e.g., a CCD camera). The space between the deflector plates and the projector lens pole piece is partially filled with a ceramic mounting, alignment, and electrical connection system integrated with the deflector plates. Other positions for the deflector system, for example within an intermediate lens system or inserted through a port in the TEM's camera chamber, are also possible. The deflector system can direct each of the images (or diffraction patterns, etc.) arising from interaction with the electron beam to a different region on a large camera (e.g., a CCD camera), thereby spatially separating the various images (or diffraction patterns, spectra, etc.) captured. The image produced by the camera then consists of an array (typically 2×2, 3×3, 4×4, 5×5, or higher dimensional or non-square array as described above) of images (or diffraction patterns, spectra, etc.) captured from different points in time.

Examples of suitable sensors, sensor arrays, detectors, or other data capture devices for electron microscope systems of the present disclosure include, but are not limited to, CCD cameras, intensified CCD cameras, CMOS image sensors, direct detection cameras (e.g., CMOS framing cameras that incorporate multiple capacitive bins for each pixel and electronic switching systems that determine which set of bins is accumulating signal at any given time), electron energy loss spectrometers (e.g. a post-column imaging filter with a CCD camera), energy-dispersive x-ray spectrometers (e.g., a silicon drift detector placed near the sample), and the like. In some embodiments, the sensors, sensor arrays, or detectors for use in the temporal compressive sensing methods of the present disclosure may further comprise a non-linear optical material, a fluorescent material, a phosphorescent material, or a micro-channel plate, that converts or amplifies the primary radiation provided by the radiation source (e.g., electrons) into a form of radiation that is directly detectable by the sensor, sensor array, or detector.

Mathematical Algorithms for Sampling and Reconstruction:

Mathematical reconstruction of the "time slice" images or datasets obtained using the disclosed compressive sensing (sampling) methods may be accomplished through the use of a variety of optimization algorithms designed to penalize non-sparse solutions of an underdetermined system of linear equations via the $l_1$ norm, the total number of non-zero coefficients, total variation, or beta process priors; an iterative greedy recovery algorithm; a dictionary learning algorithm; a stochastic Bayesian algorithm; a variational Bayesian algorithm; or any combination thereof. These algorithms vary dramatically in their details and implementations, and undoubtedly new such algorithms shall be introduced frequently in the literature, but they all fall under the following general description: algorithms for solving, or approximately solving, an underdetermined system of linear equations through the use of prior knowledge or belief that the solution is sparse or compressible in some mathematical representation, be it a representation that is known a priori, one that is purely learned from the data, or a combination of the two.

"$l_1$-optimization" refers to finding the minimum $l_1$-norm solution to an underdetermined linear system of equations, where the $l_1$-norm is the "size" of the solution vector of the linear system (i.e., the sum of the absolute values of the solution vector components) in a particular basis, for example a discrete cosine transform basis, a wavelet basis, a curvelet basis, a noiselet basis, a learned-dictionary basis, or any other basis, overcomplete or otherwise, that has been shown to induce sparse or approximately sparse representations of realistic data. It has been shown in compressive sensing theory that the minimum $l_1$-norm solution is also the sparsest possible solution under quite general conditions (Candès, E., & Romberg, J. (2005). "$l_1$-magic: Recovery of Sparse Signals via Convex Programming". URL: www.acm.caltech.edu/11magic/downloads/11magic.pdf, 4, 14; D. Donoho (2006), "For Most Large Underdetermined Systems of Linear Equations the Minimal $l_1$-norm Near Solution Approximates the Sparest Solution", Communications on Pure and Applied Mathematics 59:907-934). More generally, the $l_1$-norm in a particular basis can be used as a penalty or regularization term in a scheme that solves the underdetermined linear system of equations to within a specified error term. Often an additional penalty term involving the "total variation" (TV) is used for image data, in the context of both exact solutions and approximate solutions of the underdetermined set of linear equations. TV is typically defined as the sum of the magnitudes (typically either the $l_1$-norm or the $l_2$-norm; different authors use different definitions) of the intensity gradient vectors calculated at each point in the image. While TV is in general not technically an $l_1$-norm, its mathematical behavior is similar to that of the $l_1$-norm applied to the full set of intensity gradients, and as such a TV penalty term tends to favor a sparse intensity gradient in the solution. In other words it provides an algorithmic way to introduce a prior expectation that the gradient is sparse. This has the effect of reducing noise and favoring solutions that resemble relatively uniform regions with sharp, clearly-defined boundaries. As one of many possible examples, one may endeavor to minimize the sum of three terms: the $l_1$-norm in a discrete-cosine-transform basis, a term proportional to TV, and a term proportional to the $l_2$-norm of the error associated with the approximate solution of the underdetermined linear system of equations. It has long been known (Candès, E., & Romberg, J. (2005)) that commonly available computer algorithms, for example those associated with linear programming, can solve optimization problems of this general type efficiently.

Greedy algorithms are iterative approaches to solving systems of equations where a locally-optimal choice of candidate solutions is made at each step of the iteration based on a predefined selection rule and the addition of one of a limited set of candidate solutions to the currently existing solution. Often, a greedy algorithm will yield a locally-optimal solution that approximates a globally-optimal solution in a reasonable amount of computation time. See, for example, Cormen et al., "Greedy Algorithms", Chapter 16 in *Introduction to Algorithms*, Third Edition, MIT Press, Cambridge, Mass., 2009, for a more detailed description.

Dictionary learning approaches entail developing a "training data"-dependent transform (or dictionary) for which the solution coefficients are sparse and the basis vectors need not be orthogonal, which then allows one to solve the linear problem for a given test set of measurements. See, for example, Kreutz-Delgado et al. (2003) "Dictionary Learning Algorithms for Sparse Representation", Neural Comput. 15(2): 349-396, for a more detailed description. Some algorithms allow the dictionary to be learned directly from the compressively sensed data, with no explicit training data. Many such algorithms allow the dictionary to be refined as additional data come in. In many cases the dictionary is over-complete, i.e. there are more dictionary elements than there are dimensions in the vector space which the dictionary is meant to represent. Sparsity may still be induced reliably in such over-complete representations, for example through the use of Bayesian algorithms using beta process priors; see, for example, J. Paisley and L. Carin, "Nonparametric factor analysis with beta process priors," International Conference on Machine Learning (ICML), Montreal, Canada, 2009. We note that terminology varies; in many contexts, by definition, an over-complete dictionary is not technically referred to as a "basis," but the term "over-complete basis" is relatively common in the compressive sensing and machine learning literature. Thus for simplicity of communication in the present context we choose to use this term.

More complete descriptions of these and other algorithms for reconstructing images or other data sets from a set of measurements acquired using compressed sensing are readily available in the technical literature, see for example, Duarte et al. (2008) "Single-Pixel Imaging via Compressive Sampling", IEEE Signal Processing Magazine, March 2008, pages 83-91; and Stevens et al., (2015), "Applying Compressive Sensing to TEM Video: a Substantial Frame Rate Increase on any Camera", Adv. Structural and Chemical Imaging 1:10.

Computer Systems

Figure 9:
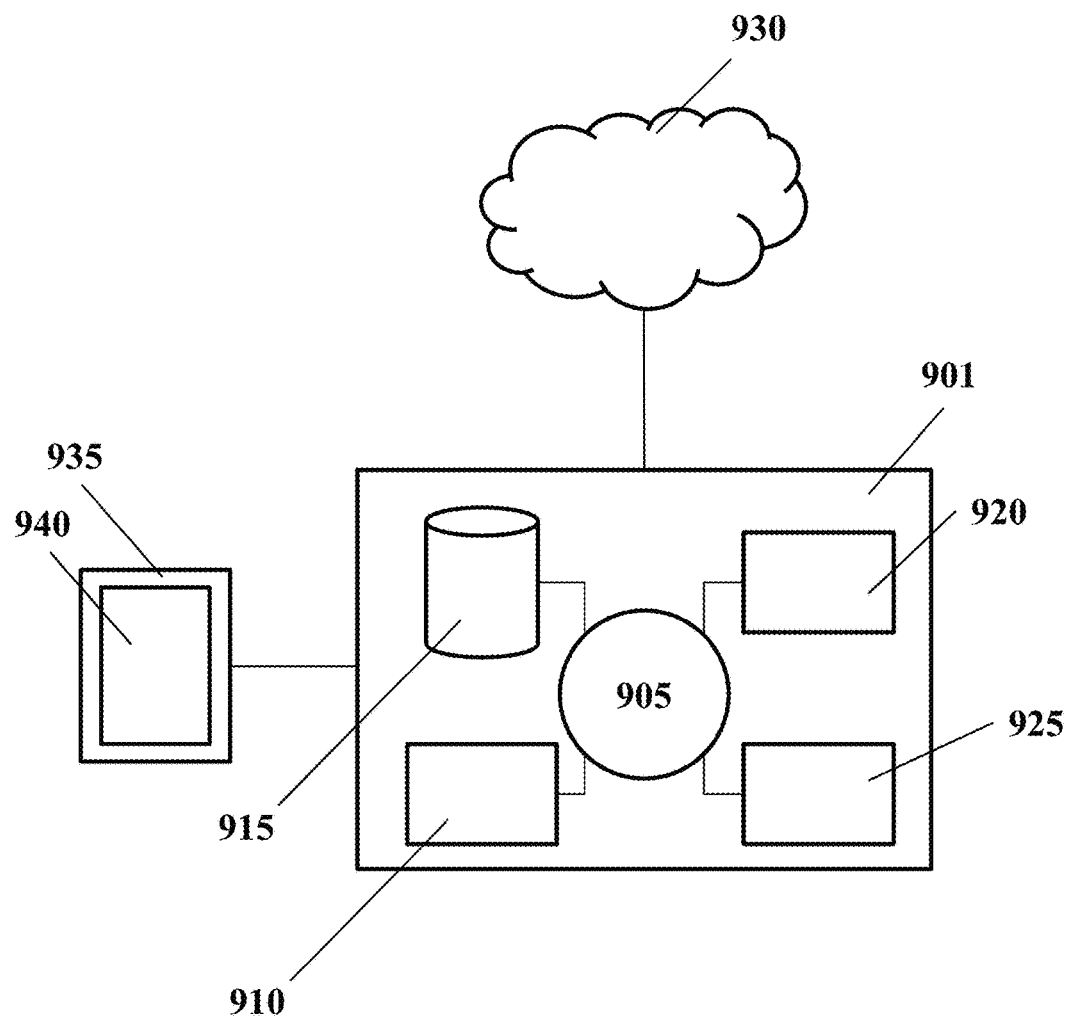
FIG. 9 illustrates one example of a computer system that may be used for implementing the temporal compressive sensing data acquisition and analysis methods of the present disclosure.

The present disclosure provides computer control systems that are programmed to implement methods of the disclosure. FIG. 9 shows a computer system 901 that includes a central processing unit (CPU, also "processor" and "computer processor" herein) 905, which can be a single core or multi core processor, or a plurality of processors for parallel processing, and may include one or more graphics processing units (GPU), or GPU-like parallel computing components, or quantum-computing components or optical computing components or electro-optical computing components. The computer system 901 also includes memory or memory location 910 (e.g., random-access memory, read-only memory, flash memory), electronic storage unit 915 (e.g., hard disk), communication interface 920 (e.g., network adapter) for communicating with one or more other systems, and peripheral devices 925, such as cache, other memory, data storage and/or electronic display adapters. The memory 910, storage unit 915, interface 920 and peripheral devices 925 are in communication with the CPU 905 through a communication bus (solid lines), such as a motherboard. The storage unit 915 can be a data storage unit (or data repository) for storing data. The computer system 901 can be operatively coupled to a computer network ("network") 930 with the aid of the communication interface 920. The network 930 can be the Internet, an internet and/or extranet, or an intranet and/or extranet that is in communication with the Internet. The network 930 in some cases is a telecommunication and/or data network. The network 930 can include one or more computer servers, which can enable distributed computing, such as cloud computing. The network 930, in some cases with the aid of the computer system 901, can implement a peer-to-peer network, which may enable devices coupled to the computer system 901 to behave as a client or a server.

The CPU 905 can execute a sequence of machine-readable instructions, which can be embodied in a program or software. The instructions may be stored in a memory location, such as the memory 910. The instructions can be directed to the CPU 905, which can subsequently program or otherwise configure the CPU 905 to implement methods of the present disclosure. Examples of operations performed by the CPU 905 can include fetch, decode, execute, and write back.

The CPU 905 can be part of a circuit, such as an integrated circuit. One or more other components of the system 901 can be included in the circuit. In some cases, the circuit is an application specific integrated circuit (ASIC).

The storage unit 915 can store files, such as drivers, libraries and saved programs. The storage unit 915 can store user data, e.g., user preferences and user programs. The computer system 901 in some cases can include one or more additional data storage units that are external to the computer system 901, such as located on a remote server that is in communication with the computer system 901 through an intranet or the Internet.

The computer system 901 can communicate with one or more remote computer systems through the network 930. For instance, the computer system 901 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 901 via the network 930.

Methods as described herein can be implemented by way of machine (e.g., computer processor) executable code stored on an electronic storage location of the computer system 901, such as, for example, on the memory 910 or electronic storage unit 915. The machine executable or machine readable code can be provided in the form of software. During use, the code can be executed by the processor 905. In some cases, the code can be retrieved from the storage unit 915 and stored on the memory 910 for ready access by the processor 905. In some situations, the electronic storage unit 915 can be precluded, and machine-executable instructions are stored on memory 910.

The code can be pre-compiled and configured for use with a machine having a processor adapted to execute the code, or can be compiled during runtime, or can be interpreted from source code during runtime without an explicit compilation step, or any combination thereof. The code can be supplied in a programming language that can be selected to enable the code to execute in a pre-compiled or as-compiled fashion.

Aspects of the systems and methods provided herein, such as the computer system 901, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 901 can include or be in communication with an electronic display 935 that comprises a user interface (UI) 940. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 905.

EXAMPLES

Example 1—Computer Simulations

Figure 3:
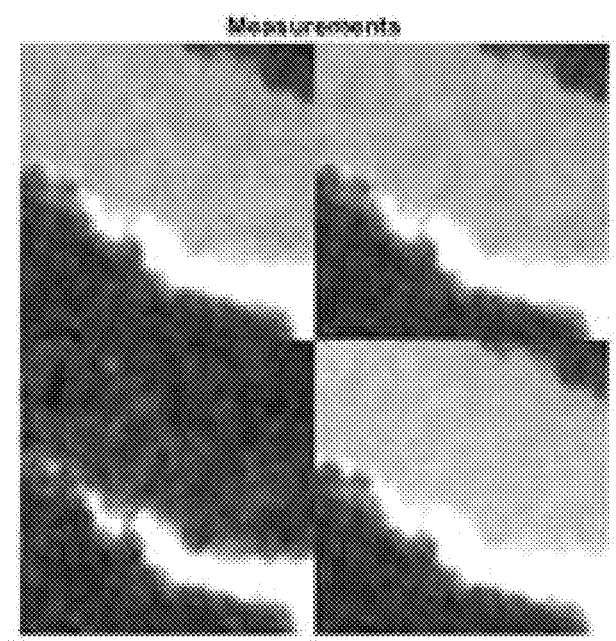
FIG. 3 illustrates four segmented image frames captured during a single camera data acquisition period using the different combinations of ten time slice datasets illustrated in FIG. 2 and a fast switching system. The four segmented image frames are captured simultaneously during a single camera data acquisition period.
Figure 4:
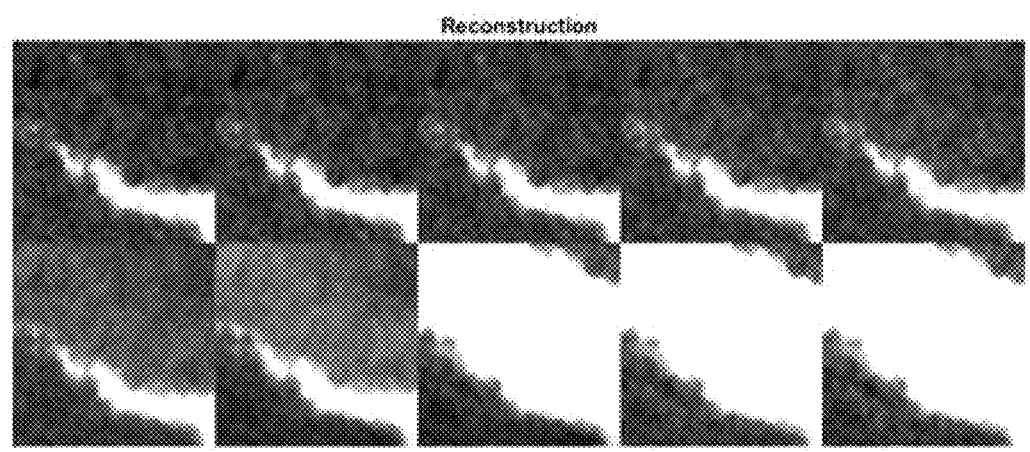
FIG. 4 illustrates the ten time slice images (datasets) reconstructed from the four segmented images illustrated in FIG. 3. The agreement between FIG. 1

Computer simulations demonstrate that a time domain-encoded temporal compressive sensing system based on the model described by equation (3) can provide reconstruction of video data with the number of time slice images significantly exceeding the number of measurement images. FIG. 1 shows 10 frames of TEM image data from an in situ tensile crack propagation experiment (courtesy K. Hattar et al., Sandia National Laboratory). Different combinations of the ten time slice images (illustrated schematically in FIG. 2) are sent to four different regions on a large area camera, for example, by using a fast beam deflection system installed in the TEM, and digitally segmented into four measurement image frames for analysis (FIG. 3). In this non-limiting example, the fast beam deflection system provides the ability to acquire 4 measurement image frames in one camera data acquisition period (i.e., during a single exposure). 16-frame fast deflector systems are already available, and compression factors much greater than the 10/4=2.5 value illustrated in this example are expected to be achievable. Application of sparse mathematical reconstruction techniques to the four measured image frames provides a reliable estimate of all ten time slice frames (FIG. 4). The same algorithm captures subtle details (e.g., changes in diffraction contrast in the stress-concentration region before failure) as well as gross discontinuities (e.g., the sudden change from time slice 7 to time slice 8). The simulation results demonstrate the reconstruction of 10 frames of video data from a single exposure period. Use of a 16 frame fast deflector system (i.e., one that captures 16 segmented image frames per camera data acquisition period) and approximately 6× compressibility, would provide approximately 100 frames of reconstructed video data per single exposure.

Example 2—TEM-Based Temporal Sensing System Using Post-Sample Deflector

Figure 5:
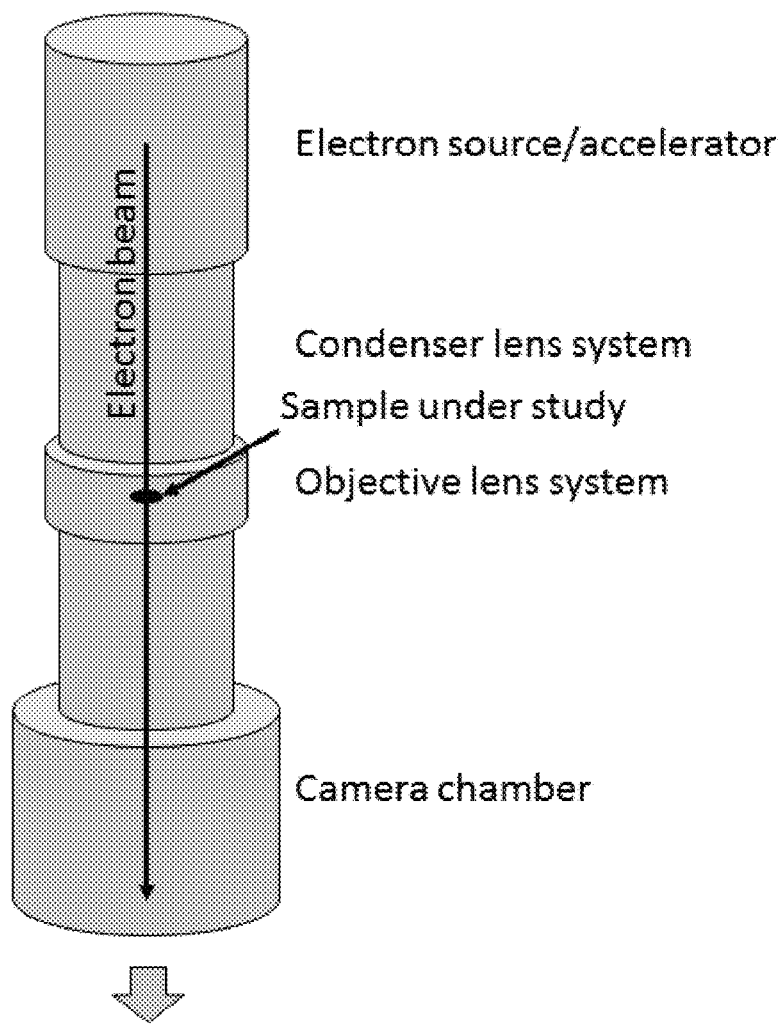
FIG. 5 depicts a generic, simplified schematic of the basic components and function of a TEM.

As an illustrative (prophetic) example, consider a TEM with a rapid, post-sample deflector system, a relatively large camera (e.g., a CCD camera with a scintillator and fiber-optic bundle, as is commonly used for TEM data acquisition), and an optional pre-sample beam blanking system. FIG. 5 shows a generic, simplified schematic of the basic components and function of a TEM. The electron source produces a beam of electrons which are accelerated to kinetic energies of typically ~80 keV to ~300 keV per electron for most current instruments. A condenser lens system focuses a selected part of the electron beam onto a sample placed near the center of an objective lens. The beam passes through the sample, and the intermediate/projector lens system produces either an image or a diffraction pattern that can be captured by a data acquisition system. The data acquisition system is typically either a camera or a post-column energy-filter system that itself includes a camera. The energy-filter system adds energy-filtered acquisition and electron energy-loss spectroscopy (EELS) capabilities to the system. Other systems (e.g., in-column energy filters) exist that produce similar results. The acquisition system includes a detector, typically but not necessarily either a CCD camera with a scintillator or a direct-detection CMOS camera or similar technology. The data acquisition rate of the system is therefore set by the acquisition and readout time of the camera (henceforth "data acquisition period" or "camera frame time").

Figure 6:
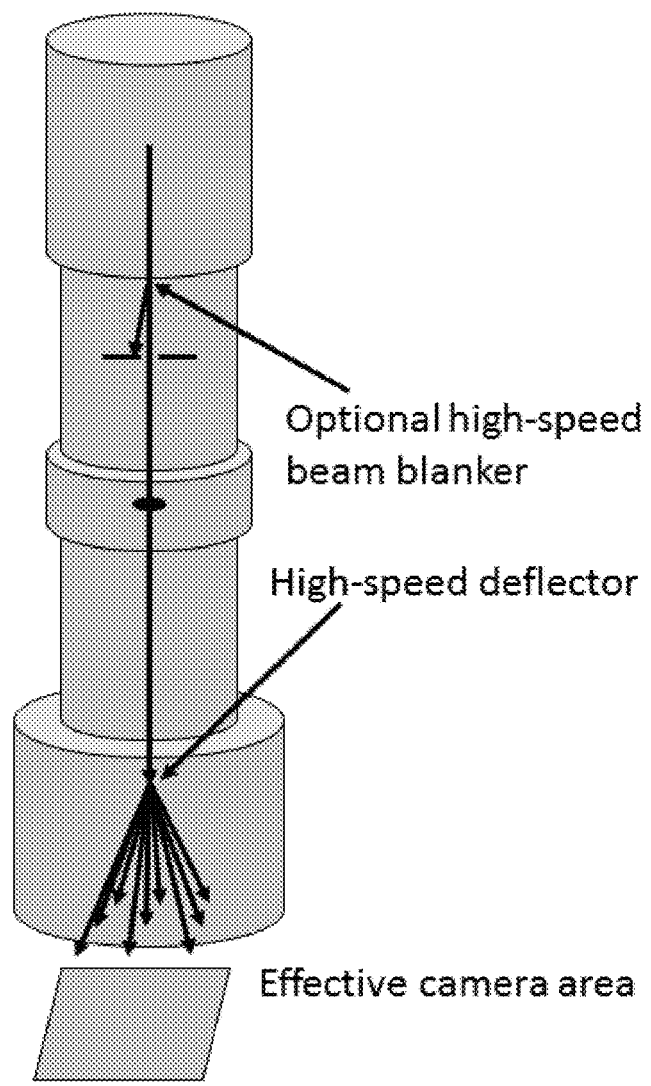
FIG. 6 illustrates one non-limiting example of a modified TEM that utilizes a high-speed deflector system to implement the compressive sensing methods disclosed herein.

FIG. 6 illustrates one non-limiting example of a TEM system that utilizes a high-speed deflector system positioned after the sample (shown here, for example, positioned after the projector lens system) that allows multiple distinct frames to be directed to (preferably, but not necessarily) non-overlapping regions of a large area camera. Operation is not fundamentally changed for a post-column energy-filtered imaging system. "High speed" in this context means the deflector can switch states many times (at least about 10 times, although preferably hundreds or thousands of times) per camera data acquisition period while introducing negligible blur. An optional high-speed beam blanker can direct the beam to an aperture while the high-speed deflector state is switching, for example positioned high in the condenser lens system (as shown), in order to reduce or eliminate blur effects.

We anticipate that a system that can switch states among a 2×2, 3×3, or 4×4 (or higher order) array of camera sub-regions with ~10 ns spent during each switching operation and ~100-1000 switching operations per camera frame time. This allows each of 10-100 or more "time slices" per camera frame time to be represented, in part, in multiple sub-regions of the camera. Mathematically, this is represented as a measurement matrix that tracks how each sub-region (or "measured frame") represents a different linear combination of time slices. The mathematical techniques associated with compressive sensing can then produce reliable estimates of all of the individual time slice datasets, with the result that ~100 distinct data frames are captured in a single camera data acquisition period.

In the case of an imaging filter, the "effective camera area" is not to be interpreted as the literal camera position but rather as an object plane that is coupled to an image plane at the actual physical camera position.

In some embodiments, instead of a rapid deflector, the system may include a solid-state multi-frame detection system, e.g., a CMOS-array framing camera having multiple storage bins per detection pixel and the ability to arbitrarily (or semi-arbitrarily) control which set of storage bins are accumulating signal at any given moment in time. Functionally the result is nearly the same; this embodiment just replaces the multi-frame switching capability of the electron optics with the multi-frame switching capability of the detector. Depending on the design of the sensor chip, such a system could operate on the mathematical model of equation (3), equation (4), or equation (5).

The deflector system illustrated in FIG. 6 may be installed after the projector lens in a TEM, for example using existing camera/detector ports. Using existing ports allows the modification to be quite non-invasive, comparable to the installation of cameras and other detectors, and the resulting system will not interfere with normal operation since the deflector can be easily retracted. As described above, the deflector is designed to laterally deflect the TEM image to any of several sub-regions of the camera's imaging sensor, for example, to any sub-region in a 4×4 array of 16 sub-regions, similar to the deflector system described for a Movie Mode Dynamic Transmission Electron Microscope (see U.S. Pat. No. 9,165,743). The deflector is preferably electrostatic rather than electromagnetic, thereby allowing existing circuit designs to switch discretely from one sensor array sub-region to another in roughly 10 nanoseconds. If the system is used to reconstruct a video with, for example, 10 µs time slices and using ~10 deflections per time slice, the duty cycle for the system is ~99%, and the blurred images from the remaining 1% of electrons should not substantially interfere with the CS reconstruction algorithms. For shorter time slices, it may be desirable to also insert a high-speed electrostatic beam blanker before the sample, thus shutting off the electron beam during the transitions and eliminating this source of blurring. For typical TEM electron gun and condenser lens system designs, the time resolution of such a system would be determined more by available beam currents and acceptable signal-to-noise ratios than by the time resolution of the deflection system itself. Thus the system would also benefit from other modifications to increase the beam current that can be delivered to the sample. Note that although this discussion has focused on real-space imaging, all TEM implementations discussed above and elsewhere in this disclosure can potentially be used for diffraction or spectroscopy as well.

Example 3—Optical Temporal Sensing System with Multiple Cameras & EOM Switching

Figure 8:
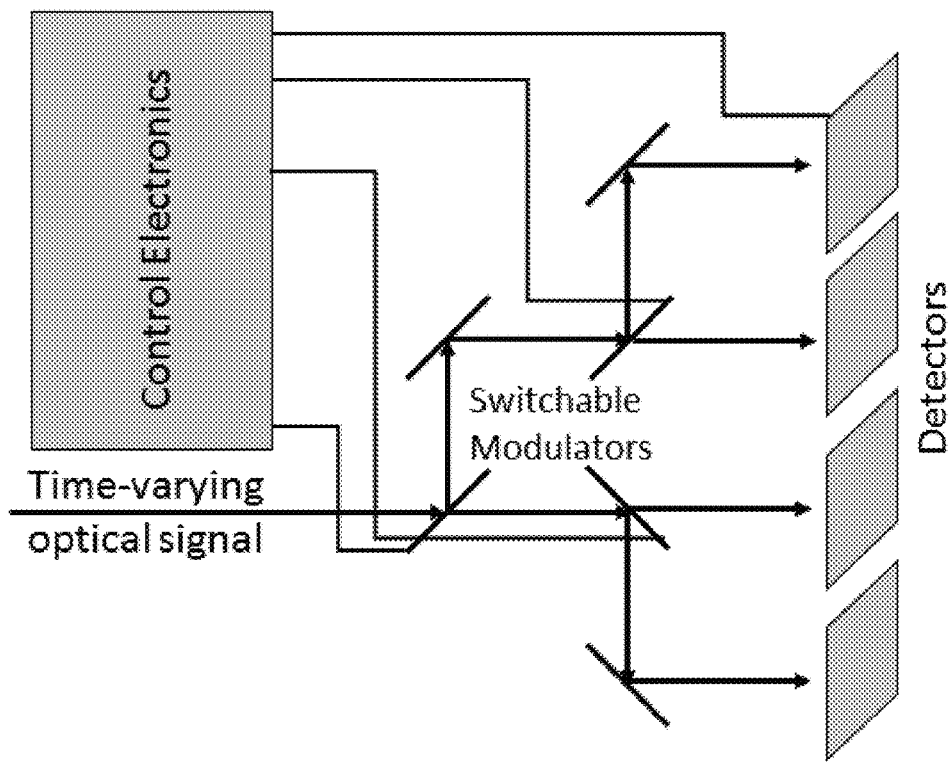
FIG. 8 illustrates one non-limiting example of an optical system (simplified schematic) for implementing the temporal compressive sensing methods disclosed herein.

As another illustrative (prophetic) example, consider a set of optical cameras with an electro-optic modulator-controlled switching network, as illustrated in FIG. 8. Electro-optic modulators (EOMs) and other high speed modulators (for example acousto-optic modulators (AOMs)) can be used to rapidly switch an optical signal between two different output paths. This switching could be implemented in a binary fashion (such that the signal goes to only one of the two output paths) or in continuous fashion (with the ability to control the fraction of signal to be sent to each output path). A network of such switches could lead to an array of detectors, each of which is a full resolution camera (or spectroscopic system) in its own right. While the engineering complexity of designing such a system for real-space imaging may be high, implementation in the field of time-resolved spectroscopy may be easier by taking advantage of well-developed EOM/AOM solutions for fiber-optic systems. A network of optical fibers and modulators would feed a parallel array of spectrometers (or a single spectrometer with a large two-dimensional sensor that can act, in effect, as a parallel array), and an electronic control system would determine what superposition of time slices is sent to each individual spectrometer. This optical system could operate in either a single-shot or a stroboscopic mode (i.e. accumulating signal over many nominally identical cycles of a process of interest), depending on the reproducibility of the sample system being measured.

Referring again to FIG. 8, temporal compressive sensing may be implemented in an optical system as illustrated for one non-limiting example. A network of electrically-controllable optical switches determines what fraction of the signal from each time slice reaches each detector. This same approach encompasses a variety of different embodiments, e.g., using free-space optics, fiber optics, or a combination of both; operating in imaging mode, spectroscopy mode, or both (spectral imaging); using electro-optical and/or acousto-optical modulators; using analog or binary modulators (if binary, their speed should be sufficient to allow many transitions per detector acquisition period); using detectors such as CCD arrays, CMOS arrays, photodiode arrays, or individual high-speed, high-sensitivity detectors such as photomultiplier tubes; wherein the network topology and the number of switches and detectors may vary.

In some embodiment, recombination of signal paths would enable interferometric operation, particularly if electrically controllable phase shifters are included. This would allow some elements of the measurement matrix to be negative, thereby providing an advantage in signal-to-noise-ratio-limited operation. It may also enable unique holographic temporal reconstruction techniques.

In some embodiment, electronic control systems may switch modulators and trigger detectors in either a predetermined sequence or an adaptive sequence (i.e. a sequence that can be modified during the acquisition on the basis of data acquired at any given time). Detectors need not all be operating at the same frequency.

As with the TEM post-sample-deflector implementation described elsewhere, the objective is to acquire data from multiple time slices within a single data acquisition period of the detector. If the data stream is highly compressible, the number of time slices reconstructed may greatly exceed the number of detectors in the system.

Example 4—Stroboscopic Ultrafast TEM

Figure 7:
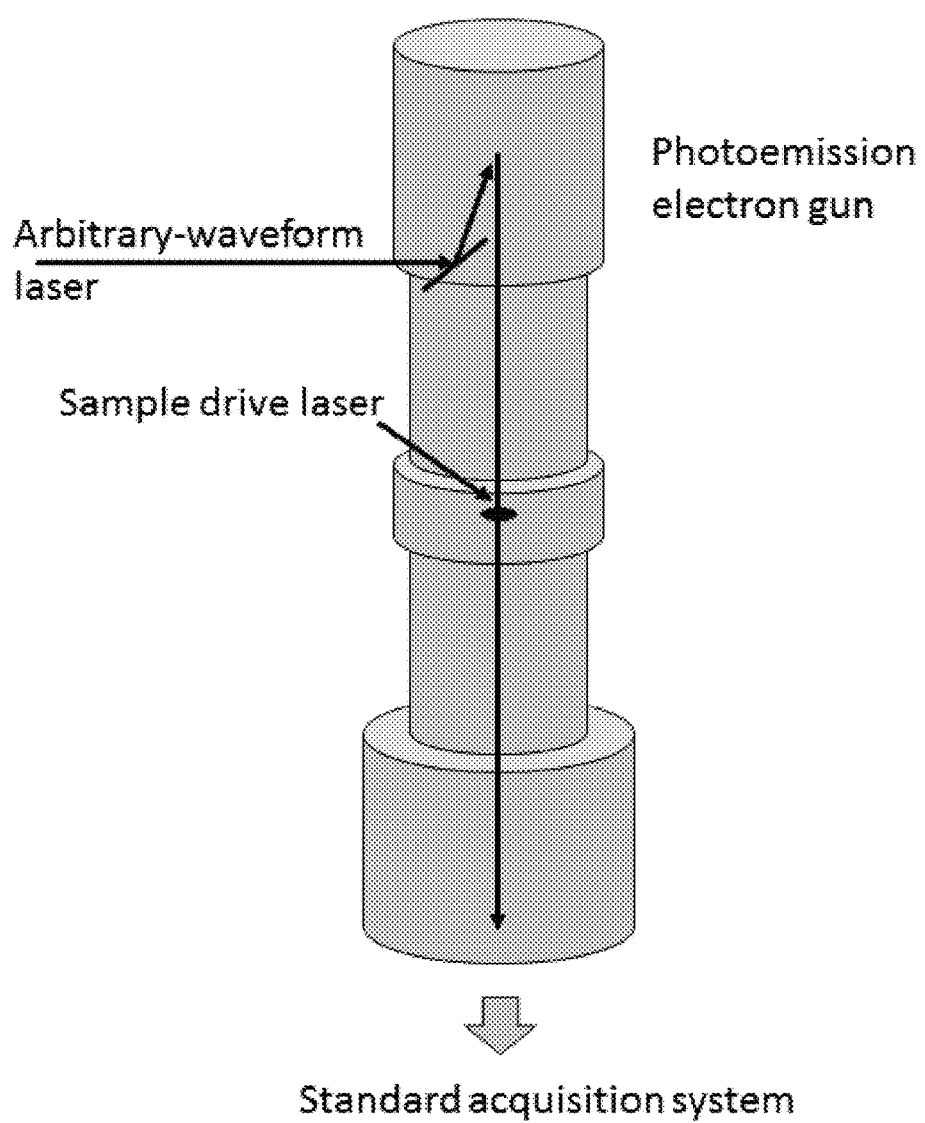
FIG. 7 illustrates one non-limiting example of a stroboscopic, time-resolved TEM that utilizes an arbitrary-waveform laser (e.g., with sub-picosecond-scale modulation and sub-nanosecond-scale pulse duration, or with nanosecond-scale modulation and microsecond-scale pulse duration) to modulate the current from a photoelectron source.

As yet another illustrative (prophetic) example, consider a stroboscopic, ultrafast TEM incorporating a picosecond-resolution arbitrary-waveform laser system as illustrated in FIG. 7. Currently, stroboscopic ultrafast TEM uses a picosecond-scale (or sub-picosecond-scale or femtosecond-scale) electron pulse as a sample probe, with one such probe pulse occurring for each cycle of some highly repeatable sample process. A time-resolved measurement is performed by accumulating data from millions of such sample process cycles, shifting the time of the probe pulse relative to the phase of the cyclic sample process, and repeating for each time slice to be measured. Measuring hundreds of such time slices can therefore require making measurements over many billions of cycles of the sample process to be studied, which may take many hours. This places extremely high demands on both the repeatability of the sample process and the stability of both the sample and measurement system. If, instead, each measurement captures data from an arbitrary superposition of time slices, and if we perform multiple measurements using such superpositions of time slices, then we have in effect implemented a temporal compressive sensing system based on equation (3). Such a system could be realized by replacing the short-pulse laser driving the TEM's cathode with an arbitrary waveform generator (AWG) laser system (similar to that described in U.S. Pat. No. 9,165,743 but operating on a different time scale), designed so as to be able to produce any specified temporal pattern of light intensity over, for example, a 200 picosecond timespan, with 1 picosecond or better resolution in the specification of the waveform. This will reduce experimental data acquisition time through two distinct effects. First, the amount of signal measured per cycle will be greatly increased. This is because the amount of current (or electrons per unit time) that can be used in such a system is limited by space-charge effects (i.e., the fact that electrons repel each other, thus causing the pulse to spread out in both space and time as it moves from the electron gun to the sample). The proposed arbitrary-waveform laser system would allow this current limit to be achieved not just for a single ~1 picosecond time slice per cycle, but for multiple such time slices. According to CS theory, the optimal data sampling throughput typically occurs at a duty cycle of ~50%, so in our example of 200 time slices (per 200 picosecond timespan), ~100 of the time slices would be filled with electron pulses while the rest would be empty. Thus the number of electrons per cycle would be roughly 100 times more, in this example, for the arbitrary-waveform system than for the single-pulse system, with no compromise in beam quality or temporal resolution. This means that ~100 times fewer measurement cycles will be required to reach acceptable signal-to-noise ratios for a given measurement. Second, the number of such measurements should also decrease, because of the inherent nature of compressive sensing such that the number, M, of measurements needed to reconstruct N time slices should be much less than N. Typically the ratio M/N is on the order of 0.1, though this varies greatly from application to application. If this ratio holds for the ultrafast TEM application, then not only should each of the M acquisitions take 100 times less total acquisition time than it would in a single-pulse-per-cycle system, but the required number of such acquisitions should be reduced by a factor of ~10, for an overall reduction in data acquisition time by a factor of about 1,000. Data sets currently requiring many hours of acquisition time could be acquired in minutes, even including the overhead needed for changing the state of the laser system. This represents a dramatic improvement in the performance of these systems.

Referring again to FIG. 7, a stroboscopic time-resolved TEM using an arbitrary-waveform laser (e.g., with sub-picosecond-scale modulation and sub-nanosecond-scale pulse duration, or with nanosecond-scale modulation and microsecond-scale pulse duration) to modulate the current from a photoelectron source may be used to implement the compressive sensing methods of the present disclosure. A second laser beam strikes the sample and initiates the process of interest. Synchronized electrical, micromechanical, or other methods of driving the sample are also possible, especially for nanosecond-scale measurements where timing-jitter requirements are easily met. The measurement of a repeatable process in the sample is repeated multiple times with different temporal modulation patterns. The mathematical reconstruction techniques of compressive sensing can then reconstruct the entire sequence of events, with the number of time slices greatly exceeding the number of distinct temporal modulation patterns. The time-averaged beam current should greatly exceed that typically used in conventional ultrafast TEM systems, because in the conventional systems the number of electrons per pulse is strictly limited by space charge effects and the necessity to keep the pulse duration at the sample as short as possible. Combining these advantages, the total acquisition time for an experiment can potentially be reduced by a factor of 1000 or more relative to conventional ultrafast TEM. This dramatically improves one of the most serious difficulties with conventional ultrafast TEM, namely the extremely long acquisition times and required stability of the sample under many millions of measurement cycles.

In other embodiments, alternative beam current modulation techniques, e.g., electrostatic modulation through rapid variation of an electrode such as an extractor electrode positioned inside the electron gun, or high-speed beam blanking at another location in the column, would produce functionally the same result. The essential point is that the beam current reaching the detector can be modulated on the time scale of the desired time slices.

Example 5—TEM System with High-Speed, Direct Detection Camera

As yet another illustrative (prophetic) example, consider a TEM system incorporating a high-speed, direct-detection camera, for example, a CMOS framing camera (e.g., a camera that can store multiple images on-chip through the use of multiple capacitive bins at each pixel and an electronic switching system that determines which set of bins is accumulating signal at any given time) with direct-electron-detection capabilities, thereby allowing it to be used for high-speed TEM applications. With appropriate chip-level electronics design, such a detector could implement the approach described by equation (3) and, with more complexity, even those described by equations (4) or (5) directly. This framing camera approach could also be used for x-ray detection and optical cameras.

All of the illustrative embodiments described above include a common feature that is distinct from previous work, i.e., a high-speed switching and/or modulation system that determines which detector or detectors selected from a plurality of detectors, or which region or regions selected from a plurality of regions on a single detector, is/are receiving information at any given time. This allows implementation of an arbitrary or semi-arbitrary "measurement matrix" of coefficients that describe the amount of signal from each time slice reaching each detector or detector sub-region. The mathematical techniques associated with compressive sensing then allow reconstruction of a number of individual time slice datasets for each data acquisition period that significantly exceeds (e.g., by 5× to 10×, or more) the number of detectors or detector sub-regions.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A system for temporal compressive sensing, comprising:
    a) a radiation source that provides radiation directed towards a sample or scene;
    b) a sensor array that detects the radiation subsequent to transmission, reflection, elastic scattering, or inelastic scattering by the sample or scene;
    c) a mechanism that rapidly modulates the one-, two-, or three-dimensional translational position or rotational orientation of the sample or scene relative to the direction of irradiation; and
    d) one or more computer processors that:
        (i) capture sensor array data for one or more data acquisition periods, wherein within each data acquisition period, one or more measurement datasets corresponding to distinct linear combinations of patterns of transmitted, reflected, elastically scattered, or inelastically scattered radiation for a series of time slices are captured; and
        (ii) reconstruct a time slice dataset for each time slice within each of the one or more data acquisition periods using:
            1) the one or more measurement datasets captured for each data acquisition period;
            2) a series of coefficients that describe a known time-dependence of the translational position or rotational orientation of the sample or scene within the data acquisition period; and
            3) an algorithm that calculates the time slice datasets from the one or more measurement datasets captured for each data acquisition period and the series of coefficients; thereby generating a series of time slice datasets for each of the one or more data acquisition periods that has a time resolution exceeding the time resolution determined by the length of the data acquisition period.

2. The system of claim 1, wherein the radiation is focused to a narrow beam and the mechanism rapidly modulates the position of the beam relative to the sample or scene.

3. The system of claim 1, wherein the radiation source is a laser, a photocathode, an electron gun, or any combination thereof.

4. The system of claim 1, wherein the sensor array is a two-dimensional sensor array comprising a charge-coupled device (CCD) sensor, a complementary metal oxide semiconductor (CMOS) sensor, a CMOS framing camera, a photodiode array, or any combination thereof.

5. The system of claim 1, wherein the sensor array further comprises a nonlinear optical material, a fluorescent material, a phosphorescent material, or a micro-channel plate, that converts the signal from the radiation source of claim 1 into radiation directly detectable by the sensor array.

6. The system of claim 1, wherein the algorithm that reconstructs the time slice datasets is an optimization algorithm that penalizes non-sparse solutions of an underdetermined system of linear equations via the h norm, the total number of non-zero coefficients, total variation, or beta process priors, an iterative greedy recovery algorithm, a dictionary learning algorithm, a stochastic Bayesian algorithm, a variational Bayesian algorithm, or any combination thereof.

7. The system of claim 1, wherein at least or at least about 10 time slice datasets are reconstructed from the one or more measured datasets captured for each data acquisition period.

8. The system of claim 1, wherein the two-dimensional sensor array operates at an effective data acquisition and read-out rate of at least or at least about 100 frames per second.

9. The system of claim 1, wherein the radiation comprises electrons and the sensor array is a charge-coupled device (CCD) sensor, an image-intensified charge-coupled device (ICCD) sensor, the detector in an electron energy loss spectrometer (EELS), a direct detection camera, or any combination thereof.

10. The system of claim 1, wherein the time slice data sets comprise reconstructed frames of transmission electron microscope image data, transmission electron microscope diffraction pattern data, transmission electron microscope electron energy loss spectral data, transmission electron microscope energy-dispersive x-ray spectral data, or scanning electron microscope image data.

11. The system of claim 1, wherein the number of time slice datasets to be reconstructed is adjusted during the calculation of the time slice datasets.

12. The system of claim 1, wherein the number of time slice datasets to be reconstructed is optimized by calculating a range of measurement matrix coefficients, each with a different number of time slices, prior to capturing the measurement datasets.

* * * * *

UNITED STATES PATENT AND TRADEMARK OFFICE
CERTIFICATE OF CORRECTION

PATENT NO. : 10,018,824 B2
APPLICATION NO. : 15/802876
DATED : July 10, 2018
INVENTOR(S) : Bryan W. Reed Page 1 of 1

It is certified that error appears in the above-identified patent and that said Letters Patent is hereby corrected as shown below:

In the Claims

In Column 32, Line 28, please replace "h norm" with -- $l_1$ norm --.

Signed and Sealed this
Twenty-eighth Day of August, 2018

Andrei Iancu
*Director of the United States Patent and Trademark Office*